US012616687B2

(12) United States Patent
Hayden et al.

(10) Patent No.: US 12,616,687 B2
(45) Date of Patent: May 5, 2026

(54) TREATMENT OF VIRAL INFECTION, DISEASE OR DISORDER USING A SELECTIVE SIR AGONIST

(71) Applicant: Prilenia Neurotherapeutics Ltd., Yakum (IL)

(72) Inventors: Michael Hayden, Yakum (IL); Michal Geva, Even-Yehuda (IL)

(73) Assignee: PRILENIA NEUROTHERAPEUTICS LTD. (IL)

( * ) Notice: Subject to any disclaimer, the term of this patent is extended or adjusted under 35 U.S.C. 154(b) by 672 days.

(21) Appl. No.: 17/980,590

(22) Filed: Nov. 4, 2022

(65) Prior Publication Data

US 2023/0100072 A1 Mar. 30, 2023

Related U.S. Application Data

(63) Continuation-in-part of application No. PCT/IL2021/050507, filed on May 4, 2021.

(60) Provisional application No. 63/019,465, filed on May 4, 2020.

(51) Int. Cl.
*A61K 31/451* (2006.01)
*A61P 31/14* (2006.01)

(52) U.S. Cl.
CPC ............ *A61K 31/451* (2013.01); *A61P 31/14* (2018.01)

(58) Field of Classification Search
CPC .............................. A61K 31/451; A61P 31/14
See application file for complete search history.

(56) References Cited

U.S. PATENT DOCUMENTS

| | | | |
|---|---|---|---|
| 10,406,145 B2 | 9/2019 | Schmidt et al. | |
| 2013/0197031 A1 | 8/2013 | Sonesson | |
| 2015/0374677 A1 | 12/2015 | Schmidt et al. | |
| 2016/0095847 A1 | 4/2016 | Sonesson | |
| 2016/0166559 A1 | 6/2016 | Sonesson | |
| 2018/0079746 A1 | 3/2018 | Oslob et al. | |
| 2019/0015401 A1 | 1/2019 | Sonesson | |
| 2019/0307722 A1 | 10/2019 | Rosa-Calatrava et al. | |
| 2020/0061076 A1* | 2/2020 | Elroy-Stein ........ | A61K 31/4184 |

FOREIGN PATENT DOCUMENTS

| | | |
|---|---|---|
| AU | 2017315783 A1 | 4/2019 |
| WO | 2012/064654 A1 | 5/2012 |
| WO | 2013/152105 A1 | 10/2013 |
| WO | 2016/003919 A1 | 1/2016 |
| WO | 2016/013813 A2 | 1/2016 |
| WO | 2016/131100 A1 | 8/2016 |
| WO | 2016/138135 A1 | 9/2016 |
| WO | 2018/039475 A1 | 3/2018 |
| WO | WO2020188558 | 9/2020 |
| WO | 2021/195470 A2 | 9/2021 |
| WO | 2021/207300 A1 | 10/2021 |

OTHER PUBLICATIONS

Alam, S. et al. (2016). Sigma-1 receptor dependent pathway for a protective endoplasmic reticulum stress response in cardiomyocytes. *Circulation Research*, 119 (Suppl. 1), A281-A281.
Allahtavakoli, M. et al. (2011). Sigma-1 receptor ligand PRE-084 reduced infarct volume, neurological deficits, pro-inflammatory cytokines and enhanced anti-inflammatory cytokines after embolic stroke in rats. *Brain Research Bulletin*, 85(3-4), 219-224.
Alon, A. et al. (2017). Identification of the gene that codes for the σ2 receptor. Proceedings of the National Academy of Sciences, 114(27), 7160-7165.
Bechill, J. et al. (2008). Coronavirus infection modulates the unfolded protein response and mediates sustained translational repression. *Journal of Virology*, 82(9), 4492-4501.
Berge, S. M. et al. (1977). Pharmaceutical salts. *Journal of pharmaceutical sciences*, 66(1), 1-19.
Cava, C. et al. (2020). In silico discovery of candidate drugs against Covid-19. *Viruses*, 12(4), 404.
Chan, C. P. et al. (2006). Modulation of the unfolded protein response by the severe acute respiratory syndrome coronavirus spike protein. *Journal of Virology*, 80(18), 9279-9287.
Chen, C. Y. et al. (2007). Open reading frame 8a of the human severe acute respiratory syndrome coronavirus not only promotes viral replication but also induces apoptosis. *The Journal of Infectious Diseases*, 196(3), 405-415.
Christ, M. G. et al. (2019). Sigma-1 receptor activation induces autophagy and increases proteostasis capacity in vitro and in vivo. *Cells*, 8(3), 211.
Dediego, M. L. et al. (2011). Severe acute respiratory syndrome coronavirus envelope protein regulates cell stress response and apoptosis. *PLoS Pathogens*, 7(10), e1002315.
Delprat, B. et al. (2020). At the crossing of ER stress and MAMs: a key role of sigma-1 receptor ?. *Calcium Signaling*, 699-718.
Dryden J. (2020). "Study to evaluate antidepressant as potential COVID-19 treatment", Washington University School of Medicine in St. Louis, Retrieved from: URL: < https://medicine.wustl.edu/news/study-to-evaluate-antidepressant-as-potential-covid-19-treatment/>.
Fung, T. S. et al. (2014). Coronavirus infection, ER stress, apoptosis and innate immunity. *Frontiers in Microbiology*, 5, 296.
Gassen, N. C. et al. (2019). SKP2 attenuates autophagy through Beclin1-ubiquitination and its inhibition reduces MERS-Coronavirus infection. Nature Communications, 10(1), 1-16.
Gordon, D. E. et al. (2020). A SARS-COV-2 protein interaction map reveals targets for drug repurposing. *Nature*, 583(7816), 459-468.
Harapan, H. et al. (2020). Coronavirus disease 2019 (COVID-19): A literature review. *Journal of Infection and Public Health,* 13(5), 667-673.

(Continued)

*Primary Examiner* — Timothy R Rozof
(74) *Attorney, Agent, or Firm* — Mark S. Cohen; PEARL COHEN ZEDEK LATZER BARATZ LLP

(57) ABSTRACT

The subject invention provides a method for treating, reducing the incidence, suppressing or inhibiting a viral infection, disease, disorder or symptoms thereof in a subject in need thereof comprising administering to the subject a selective S1R agonist. In another aspect, the viral disease is COVID-19, and the selective S1R agonist is pridopidine or pharmaceutically acceptable salt thereof.

18 Claims, 9 Drawing Sheets

(56) References Cited

OTHER PUBLICATIONS

International Search Report and Written Opinion of the International Searching Authority dated Jul. 12, 2021, issued in the corresponding PCT International Application No. PCT/IL2021/050507, dated May 4, 2021.
Johnston, T. H. et al. (2019). Pridopidine, a clinic-ready compound, reduces 3, 4-dihydroxyphenylalanine-induced dyskinesia in Parkinsonian macaques. *Movement Disorders*, 34(5), 708-716.
Jose, R. J. et al. (2020). COVID-19 cytokine storm: the interplay between inflammation and coagulation. *The Lancet Respiratory Medicine*, 8(6), e46-e47.
Kim, S. J. et al. (2018). The essential role of mitochondrial dynamics in antiviral immunity. *Mitochondrion*, 41, 21-27.
Li, Q. et al. (2005). The interaction of the SARS coronavirus non-structural protein 10 with the cellular oxido-reductase system causes an extensive cytopathic effect. Journal of Clinical Virology, 34(2), 133-139.
Li, S. et al. (2020). Regulation of the ER stress response by the ion channel activity of the infectious bronchitis coronavirus envelope protein modulates virion release, apoptosis, viral fitness, and pathogenesis. *Frontiers in Microbiology*, 10, 3022.
Liao, Y. et al. (2013). Upregulation of CHOP/GADD153 during coronavirus infectious bronchitis virus infection modulates apoptosis by restricting activation of the extracellular signal-regulated kinase pathway. *Journal of Virology*, 87(14), 8124-8134.
Liao, K. et al. (2016). Cocaine-mediated induction of microglial activation involves the ER stress-TLR2 axis. *Journal of Neuroinflammation*, 13(1), 1-16.
Longhitano, L. et al. (2017). Sigma-1 and Sigma-2 receptor ligands induce apoptosis and autophagy but have opposite effect on cell proliferation in uveal melanoma. *Oncofarget*, 8(53), 91099.
Maurice, T. et al. (1994). Behavioral evidence for a modulating role of σ ligands in memory processes. I. Attenuation of dizocilpine (MK-801)-Induced amnesia. *Brain Research*, 647(1), 44-56.
Minakshi, R. et al. (2009). The SARS Coronavirus 3a protein causes endoplasmic reticulum stress and induces ligand-independent downregulation of the type 1 interferon receptor. *PloS One*, 4(12), e8342.
Nabirotchkin, S. et al. (2020). Focusing on the unfolded protein response and autophagy related pathways to reposition common approved drugs against COVID-19. Distributed under a Creative Commons CC BY. Retrieved from: URL: chrome-extension://efaidnbmnnnibpcajpcglolefindmkaj/https://pdfs.semanticscholar.org/d4df/5234c16c0e838f8e39ed0ea5576a5a474081.pdf.
Sileikyte, J. et al. (2019). The mitochondrial permeability transition in mitochondrial disorders. *Oxidative Medicine and Cellular Longevity*, 2019.
Starkov, A. A. (2008). The role of mitochondria in reactive oxygen species metabolism and signaling. *Annals of the New York Academy of Sciences*, 1147(1), 37-52.
Tesei, A. et al. (2018). Sigma receptors as endoplasmic reticulum stress "gatekeepers" and their modulators as emerging new weapons in the fight against cancer. *Frontiers in Pharmacology*, 9, 711.
Tesei, A. et al. (2019). Anti-tumor efficacy assessment of the sigma receptor pan modulator RC-106. A promising therapeutic tool for pancreatic cancer. *Frontiers in Pharmacology*, 10, 490.
Vela, J. M. (2020). Repurposing sigma-1 receptor ligands for COVID-19 therapy ?. *Frontiers in Pharmacology*, 11, 582310.
Wang, J. Z. et al. (2020). An anti-oxidative therapy for ameliorating cardiac injuries of critically ill COVID-19-infected patients. *International Journal of Cardiology*, 312, 137.
Weng, T. Y. et al. (2017). Roles of sigma-1 receptors on mitochondrial functions relevant to neurodegenerative diseases. *Journal of Biomedical Science*, 24(1), 1-14.
Zhao, J. et al. (2014). Sigma receptor ligand,(+)-pentazocine, suppresses inflammatory responses of retinal microglia. *Investigative Ophthalmology & Visual Science*, 55(6), 3375-3384.
Clinicaltrials.Gov: "A Double-blind, Placebo-controlled Clinical Trial of Fluvoxamine for Symptomatic Individuals With COVID-19 Infection", Apr. 13, 2020 (Apr. 13, 2020), pp. 1-8, XP055928475, Retrieved from the Internet: URL:https://clinicaltrials.gov/ct2/show/NCT04342663 [retrieved on Jun. 7,2022].
Kulkarni et al. "On the mechanism of antidepressant-like action of berberine chloride" European Journal of Pharmacology. Jul. 28, 2008;589(1-3):163-72.
Li et al. "Existing bitter medicines for fighting 2019-nCOV-associated infectious diseases" The FASEB Journal. May 2020;34(5):6008-16.
Li, Y. L., et al. "Investigated potential traditional Chinese medicinal ingredients in treatment on COVID-19 based on database.", 2020; Abstract.
Maurice et al. "The pharmacology of sigma-1 receptors" Pharmacology & therapeutics. Nov. 1, 2009;124(2):195-206.
Ostrov et al. "Highly specific sigma receptor ligands exhibit antiviral properties in SARS-CoV-2 infected cells" Pathogens. Nov. 20, 2021;10(11):1514.
Schafer et al. "Repurposing potential of 1st generation H1-specific antihistamines as anti-filovirus therapeutics" Antiviral research. Sep. 1, 2018;157:47-56.
Smieszek et al. "Amantadine disrupts lysosomal gene expression; potential therapy for COVID19" BioRxiv. Apr. 5, 2020:2020-04.
Su et al. "The sigma-1 receptor as a pluripotent modulator in living systems" Trends in pharmacological sciences. Apr. 1, 2016;37(4) 262-78.
Supplementary European Search Report issued for European Application No. EP21799724.6 dated Apr. 23, 2024.
Vahabzadeh et al. "Noscapine modulates neuronal response to oxygen-glucose deprivation/reperfusion injury via activation of sigma-1 receptor in primary cortical cultures" Iranian Journal of Pharmaceutical Research: IJPR. 2020;19(1):331.
Zhiyoung S. et al. "Novel coronavirus and cardiovascular disease—Advances in the diagnosis and treatment of novel coronavirus pneumonia (COVID-19) infection complicated by hypertension", 2020; Chin J Evid Based Cardiovasc Med, vol. 12, No. 4.

* cited by examiner

TREATMENT OF VIRAL INFECTION, DISEASE OR DISORDER USING A SELECTIVE SIR AGONIST

CROSS REFERENCE TO RELATED APPLICATIONS

This application is a Continuation-in-Part Application from International Application No. PCT/IL2021/050507 filed 4 May 2021 which claims the benefit of U.S. Ser. No. 63/019,465, filed on 4 May 2020 which are incorporated in their entirety herein by reference.

FIELD OF THE INVENTION

The subject invention provides a method for treating, reducing the incidence, suppressing or inhibiting a viral infection, disease, disorder or symptoms thereof in a subject in need thereof, comprising administering to the subject a selective S1R agonist. In another aspect, the viral disease is COVID-19, and the selective S1R agonist is pridopidine or a pharmaceutically acceptable salt thereof.

BACKGROUND OF THE INVENTION

Coronavirus disease 2019 or COVID-19 has rapidly emerged as a global pandemic. As of end of April 2021 there are nearly 150 million confirmed cases and over 3 million deaths in more than 100 countries. There are a small number of treatments which received emergency approval, and vaccinations have only recently become available. Coronaviruses have a single-stranded RNA genome and encode for many similar proteins. Protein and RNA replication machinery are the classic targets for antiviral drugs in development for the past years. However, the lifecycle of coronaviruses relies on several host-cell encoded cellular pathways (Nabirotchkin et al. 2020). Among these pathways are the ER-stress Unfolded Protein Response (UPR), autophagy and Mitochondrial function.

A recent bioinformatic/proteomic analysis (Gordon et al. 2020) identified SARS-CoV-2 proteins that interact with the human Sigma-1 and Sigma-2 receptors (S1R/S2R) and contribute to the development of the disease. This highlights sigma receptors as a potential drug target for treating COVID-19. Of the ~20 viral-encoded proteins, Nsp6 and Or19c were identified as directly interacting with Sigma receptors.

The S1R is an ER chaperone protein located at the mitochondrial associated membranes (MAM) that plays a key role in ER-mitochondrial interactions. S1R regulates ER stress, mitochondrial function, calcium signaling, autophagy and cellular homeostasis (Weng, Tsai, and Su 2017; Delprat et al. 2020). S1R deletion enhances ER stress and oxidative stress while S1R overexpression and activation by different agonists restores cellular homeostasis and enhances survival. S1R activation is shown to reduce ER stress, restore mitochondrial function and enhance autophagy (Tesei et al. 2018; Maurice et al. 1994; Christ et al. 2019).

The S2R is an intracellular chaperon protein which was recently cloned and identified as TMEM97 (Alon et al. 2017). Although the S1Rs and the S2Rs are not genetically related, they share a similar pharmacological profile and some S1R ligands also show high affinity towards the S2R including haloperidol and DTG, (Longhitano et al. 2017; Tesei et al. 2018; Katnik et al. 2006) Several S2R ligands are shown to induce apoptosis, which makes them attractive anti-cancer drugs (Tesei et al. 2019).

Several Sigma ligands were recently reported to show anti-viral activity (Gordon et al. 2020). The Sigma ligands that demonstrated anti-viral activity (measuring viral titer assay) included hydroxychloroquine, Clemastine and Haloperidol. All these compounds show high affinity for the S1R as well as high affinity for the S2R, thus all are non-selective compounds. Ki for S1R vs S2R: hydroxychloroquine is 200 nM and 800 nM respectively, Clemastine S1R Ki is 10 nM vs 20 nM for S2R, and Haloperidol has S1R Ki of 4 nM vs S2R Ki of 54 nM.

Gordon in his manuscript presents anti-viral activity with hydroxychloroquine, Clemastine and Haloperidol (Gordon et al. 2020). Hydroxychloroquine anti-viral activity demonstrated at ~2 uM which was associated with ~30% reduction in cell viability (Gordon et al. 2020). The effective Clemastine dose for anti-viral activity is 10 uM, and this dose is also associated with ~40% cell death. Similarly, Haloperidol's anti-viral effect was demonstrated at 100 uM, with ~30% cell death (Gordon et al. 2020).

Pridopidine (4-[3-(methylsulfonyl)phenyl]-1-propyl-piperidine) is a highly selective S1R ligand with Ki=0.57 nM and S2R Ki of 5450 nM (Johnston et al. 2019). Thus, pridopidine has 95-fold higher affinity for the S1R vs the S2R and is the most selective S1R ligand.

SUMMARY OF THE INVENTION

In the first aspect, the invention provides a method for treating, reducing the incidence, suppressing or inhibiting a viral infection, disease, disorder or symptoms thereof in a subject in need thereof comprising administering to the subject a composition comprising a selective S1R agonist.

In a further aspect the invention provides a method of reducing endoplasmic reticulum stress (ER stress) due to a viral infection, disease or disorder in a subject, comprising administering to the subject a composition comprising a selective S1R agonist.

In a further aspect the invention provides a method for treating, reducing the incidence, suppressing or inhibiting a human coronavirus or its symptoms or mutation thereof in a subject in need thereof comprising administering to the subject a composition comprising a selective S1R agonist.

In a further aspect the invention provides a method for treating, reducing the incidence, suppressing or inhibiting a viral infection, disease, disorder or symptoms thereof in a subject in need thereof comprising administering a composition comprising pridopidine, its pharmaceutically acceptable salt, its deuterated analog or combination of pridopidine and at least one of its analog compounds 1-7, or salts thereof:

(1)

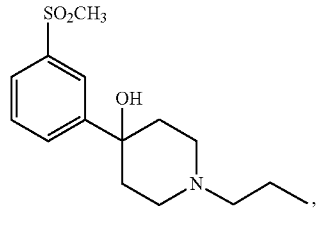

,

-continued

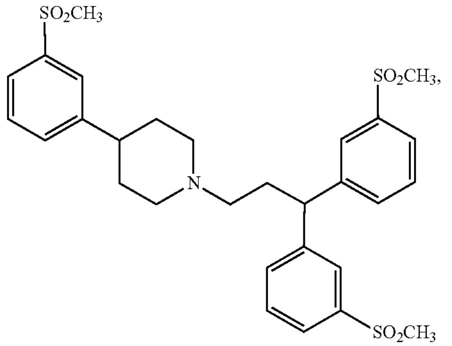

(2)

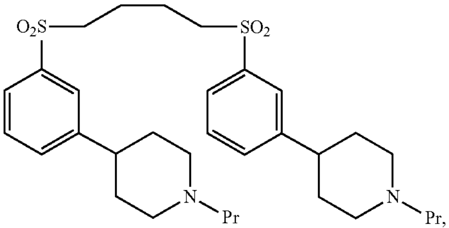

(3)

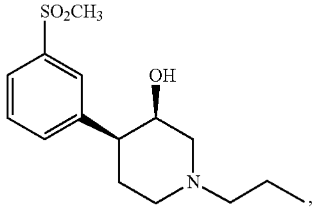

(4)

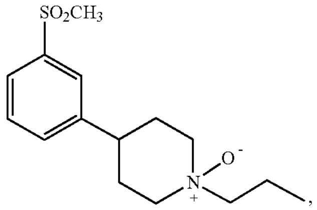

(5)

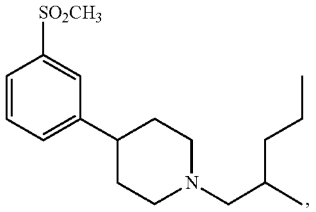

, or (6)

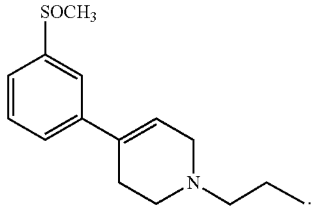

(7)

In some embodiments the viral infection, disease or disorder comprise human coronavirus, Severe acute respiratory syndrome (SARS), Middle East Respiratory Syndrome (MERS) coronavirus, SARS coronavirus 2 (SARS-CoV-2) or mutations therefrom. In other embodiments, the disease is COVID-19.

In some embodiments, the methods of this invention make use of a selective S1R agonist. In another embodiment, the selective S1R agonist is pridopidine, its pharmaceutically acceptable salt, its deuterated analog or combination of pridopidine and at least one of its analog compounds 1-7, or salts thereof.

In some embodiments, said pridopidine is in its neutral/base form. In some embodiments, said pridopidine is in a pharmaceutically acceptable salt form. In some further embodiments, said pridopidine is pridopidine hydrochloride.

In some embodiments, the composition comprising the selective S1R agonist is administered orally. In some embodiments, the composition comprising pridopidine, its pharmaceutically acceptable salt, its deuterated analog or combination of pridopidine and at least one of its analog compounds 1-7, or salts thereof is administered orally.

In other embodiments, the composition is administered via systemic administration. In another embodiment, the composition is administered via oral administration. In another embodiment, the composition is formulated as an oral liquid, solid, semi-solid dosage form, injectable, dermal/transdermal dosage form, ophthalmic dosage forms, inhalable compositions. In another embodiment, the composition is formulated as an inhalable powder, an injectable, a liquid, a gel, a solid, a capsule, eye drops or a tablet.

In some embodiments, the composition is administered periodically (i.e. said pridopidine is administered at regular pre-determined intervals of time, such as on a daily, hourly, weekly, monthly periods, each optionally also defining the dose to be administered and the number of administrations per time period). In further embodiments, the composition is administered once daily, twice daily or three times a day. In further embodiments, the composition is administered less often than once daily. In some embodiments, the composition is administered in one dose, two doses or three doses per day.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE PRESENT INVENTION

Figure 1:
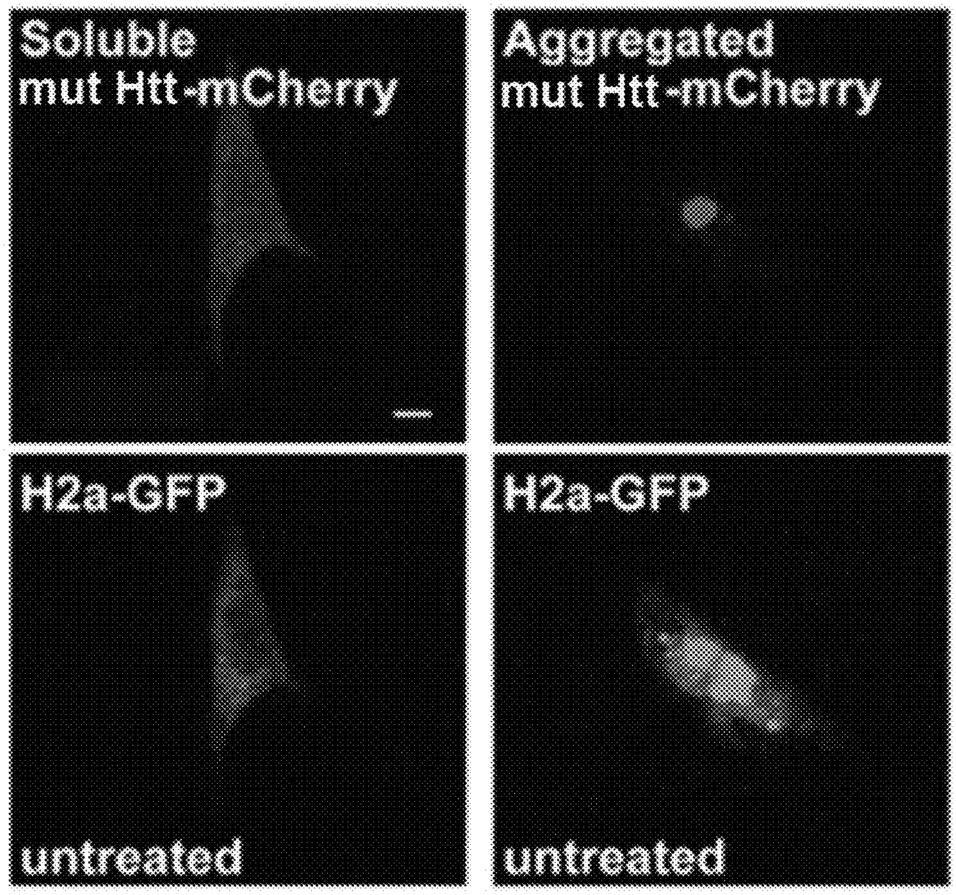
FIG. 1 shows representative images, demonstrating that mutant Htt (mHtt) results in ER stress (H2a-GFP) by pridopidine which is quantified by H2a-GFP aggregation. Early ER stress is quantified with H2a-GFP, a protein indicator which, in response to ER stress, accumulates to form aggregates. H2a-GFP was transiently co-expressed with wild-type (WT, Htt20Q)-mCherry or mutant (Htt96Q)-mCherry (exon 1) in STHdhQ7/7 cells. Cells were treated without or with increasing concentrations of pridopidine (from 0.03 to 3 μM) starting 4 h post-transfection and imaged in a confocal microscope 24 h post-transfection. Images of individual cells (~150 cells per experiment) with Htt96Q-mCherry aggregates or with Htt20Q-mCherry were quantified compared to untreated cells with and without aggregates.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the first aspect the invention provides a method for treating, reducing the incidence suppressing or inhibiting a viral infection, disease, disorder or symptoms thereof in a subject in need thereof comprising administering to the subject a composition comprising a selective S1R agonist.

In a further aspect the invention provides a method for treating, reducing the incidence, suppressing or inhibiting a viral infection, disease, disorder or symptoms thereof in a subject in need thereof comprising administering a composition comprising pridopidine, its pharmaceutically acceptable salt, its deuterated analog or combination of pridopidine and at least one of its analog compounds 1-7, or salts thereof:

(1)

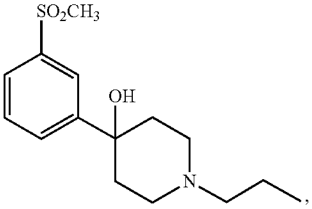

, (2)

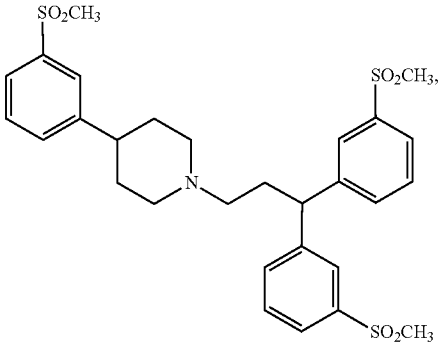

(3)

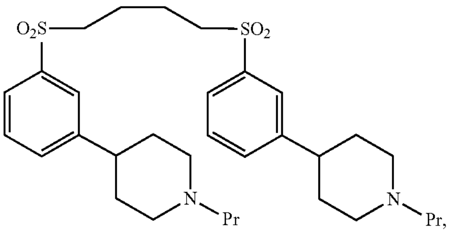

(4)

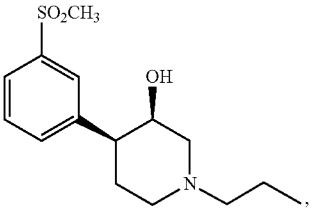

, (5)

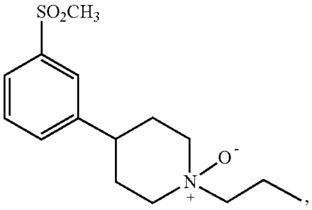

,

-continued (6)

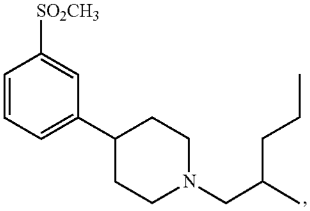

, or (7)

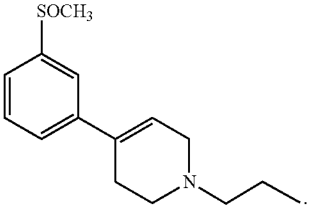

.

When referring to a "viral infection, disease, disorder or any symptom thereof" it should be understood to encompass any type of condition that risks the health of a subject wherein the viral infection plays a direct or indirect role.

In some embodiments the viral infection, disease or disorder comprise human coronavirus, Severe acute respiratory syndrome (SARS), Middle East Respiratory Syndrome (MERS) coronavirus, SARS coronavirus 2 or mutations therefrom. In other embodiments, the disease is COVID-19 by administering a composition comprising a selective S1R agonist.

In one embodiment, this invention provides a method of treating, reducing the incidence, suppressing or inhibiting a human coronavirus or its mutations and/or symptoms thereof by administering a composition comprising a selective S1R agonist In one embodiment, this invention provides a method of treating, reducing the incidence, suppressing or inhibiting a severe acute respiratory syndrome (SARS), or its mutations and/or symptoms thereof by administering a composition comprising a selective S1R agonist.

In one embodiment, this invention provides a method of treating, reducing the incidence, suppressing or inhibiting a Middle East Respiratory Syndrome (MERS) coronavirus, or its mutations and/or symptoms thereof by administering a composition comprising a selective S1R agonist.

In one embodiment, this invention provides a method of treating, reducing the incidence, suppressing or inhibiting a SARS coronavirus 2 (SARS-CoV-2), or its mutations and/or symptoms thereof by administering a composition comprising a selective S1R agonist.

In one embodiment, this invention provides a method of treating, reducing the incidence, suppressing or inhibiting COVID-19, or its mutations and/or symptoms thereof by administering a composition comprising a selective S1R agonist.

In one embodiment, this invention provides a method of reducing ER stress due to a viral infection, disease or disorder in a subject. In another embodiment, the viral infection, disease or disorder comprises human coronavirus, SARS, MERS coronavirus, SARS coronavirus 2, or mutations thereof and/or symptoms thereof. In another embodiment, the disease is COVID-19 by administering a composition comprising a selective S1R agonist.

In some embodiment, this invention provides a method for treating, reducing the incidence, suppressing or inhibiting a Middle East Respiratory Syndrome (MERS) coronavirus, or its mutations and/or symptoms thereof by administering a composition comprising a selective S1R agonist. In other embodiment, the symptoms comprise renal failure, fever, tiredness, dry cough, aches and pains, nasal congestion, runny nose, sore throat, diarrhea or combination thereof.

The most common symptoms of COVID-19 are fever, dry cough, and tiredness. Some patients may have aches and pains, nasal congestion, sore throat or diarrhea. These symptoms are usually mild and begin gradually. Some people become infected but only have very mild symptoms. Most people (about 80%) recover from the disease without needing hospital treatment. Around 1 out of every 5 people who gets COVID-19 becomes seriously ill and develops difficulty breathing. Older people, and those with underlying medical problems like high blood pressure, heart and lung problems, diabetes, or cancer, are at higher risk of developing serious illness. However, anyone can catch COVID-19 and become seriously ill. Even people with very mild symptoms of COVID-19 can transmit the virus. People of all ages who experience fever, cough and difficulty breathing should seek medical attention.

In some embodiment, this invention provides a method for treating, reducing the incidence, suppressing or inhibiting COVID-19 by administering a composition comprising a selective S1R agonist. In other embodiment, the symptoms comprise renal failure, fever, tiredness, dry cough, aches and pains, nasal congestion, runny nose, sore throat, diarrhea or combination thereof.

In some embodiments, the methods of this invention, make use of a composition comprising a selective S1R agonist. In other embodiments, the S1R agonist is pridopidine, its pharmaceutically acceptable salt, its deuterated analog or combination of pridopidine and at least one of its analog compounds 1-7, or salts thereof.

The SAR-CoV-2 Infection Induces the ER Stress Unfolder Protein Response (UPR)/Autophagy Pathway is Essential for the Life Cycle of the Coronavirus:

In response to a viral invasion the host cell activates the unfolded protein response (UPR) in an attempt to restore homeostasis of the endoplasmic reticulum (ER) by global protein translation shut down.

Induction of the UPR by coronavirus invasion constitutes a major aspect of the virus-host cell interaction. ER stress and UPR activation contribute significantly to the viral replication and pathogenesis during coronavirus infection (Fung and Liu 2014).

The virus manipulates the UPR to complete its life cycle and enhance its propagation (Cava, Bertoli, and Castiglioni 2020). Reduction of ER stress makes it is therefore an attractive candidate target for anti-viral therapies.

Previously identified coronaviruses such as SARS-CoV and MERS-CoV have been shown to induce ER stress, utilizing the ER for viral replication, and interfering with apoptotic pathways to ensure continued viral replication (S. Li et al. 2020; DeDiego et al. 2011). SARS-CoV induction of the UPR has been suggested to selectively modulate its functions to enhance its replication while avoiding apoptosis (Chan et al. 2006).

Viral infection-induced ER stress leads to the phosphorylation of eIF2α, which inhibits global translation in the cell, but increases translation of UPR relevant genes, such as ATF4 and CHOP (Bechill et al. 2008; K. Liao et al. 2016).

In some embodiments, a selective S1R agonist reduces the ER stress in a patient afflicted with a viral infection, disease or disorder. In other embodiment, the selective S1R agonist is pridopidine, its pharmaceutically acceptable salt, its deuterated analog or combination of pridopidine and at least one of its analog compounds 1-7, or salts thereof.

The UPR pathway together with the autophagy pathway, are essential for viral infection, regulating protein homeostasis, innate immunity and clearance of viral particles. For example, the coronavirus MERS-CoV blocks the autophagy pathway (Gassen et al. 2019).

In some embodiments, a selective S1R agonist regulates ER-stress and the UPR pathway in a patient afflicted with a viral infection, disease or disorder. In another embodiment the selective S1R agonist reduces ER-stress. In other embodiment, the selective S1R agonist is pridopidine, its pharmaceutically acceptable salt, its deuterated analog or combination of pridopidine and at least one of its analog compounds 1-7, or salts thereof.

In some embodiment, a selective S1R agonist regulates the autophagy pathway in a patient afflicted with a viral infection, disease or disorder. In other embodiment, the selective S1R agonist is pridopidine, its pharmaceutically acceptable salt, its deuterated analog or combination of pridopidine and at least one of its analog compounds 1-7, or salts thereof.

Oxidative Stress and Mitochondrial Dysfunction in COVID-19

Mitochondria have a key role in controlling ROS levels, and dysfunctional mitochondria produce high, uncontrolled levels of toxic ROS (excessive ROS levels cause extensive damage to cells and oxidize proteins). Specifically, it is shown that SARS-CoV2 infection enhances ROS levels, primarily due to activity of the immune system (Wang, Zhang, and Bai 2020; Starkov 2008). The ORF8 protein of SARS-CoV localizes to the mitochondria, where it causes an increase in ROS production, indicating its role in regulating ROS production and mitochondrial function (Chen et al. 2007) In light of this, treatments that can reduce ROS are potential targets for COVID-19.

In some embodiments, a selective S1R agonist reduces ROS in a patient afflicted with a viral infection, disease or disorder. In other embodiment, the selective S1R agonist is pridopidine, its pharmaceutically acceptable salt, its deuterated analog or combination of pridopidine and at least one of its analog compounds 1-7, or salts thereof.

Patients infected with SARS-CoV-2 have high plasma levels of pro-inflammatory cytokines, including IL-1β, IL-2, TNFα, MCP1, IL7 and GSCF (Harapan et al. 2020). Increased cytokine levels is a common complication of respiratory illnesses, in which overproduction of early response proinflammatory cytokines can lead to severe complications, including multiorgan failure and death (Ricardo J Jose and Manuel 2020). Patients in the ICU have significantly higher levels of GSCF, MCP1 and TNFα, suggesting that the cytokine storm may be an underlying cause for disease severity. Treatment with S1R agonists have been shown to decrease cytokine levels and suppress the inflammatory response (Zhao et al. 2014; Allahtavakoli and Jarrott 2011).

In some embodiment, a selective S1R agonist reduces cytokine plasma levels in a patient afflicted with a viral infection, disease or disorder. In other embodiment, the selective S1R agonist is pridopidine, its pharmaceutically acceptable salt, its deuterated analog or combination of pridopidine and at least one of its analog compounds 1-7, or salts thereof.

Compositions for Use in the Methods of this Invention

In some embodiments, this invention provides a composition comprising a selective S1R agonist for use in the methods of this invention. In some embodiments, this invention provides a composition comprising pridopidine, its pharmaceutically acceptable salt, its deuterated analog or combination of pridopidine and at least one of its analog compounds 1-7, or salts thereof for use in the methods of this invention.

In some embodiments, this invention provides a composition comprising a selective S1R agonist for use in treating, reducing the incidence, suppressing or inhibiting a viral infection, disease, disorder or symptoms thereof in a subject in need thereof.

In some embodiments, this invention provides a composition comprising pridopidine, its pharmaceutically acceptable salt, its deuterated analog or combination of pridopidine and at least one of its analog compounds 1-7, or salts thereof for use in treating, reducing the incidence, suppressing, or inhibiting a viral infection, disease, disorder, or symptoms thereof in a subject in need thereof.

In some embodiments, this invention provides a composition comprising pridopidine, its pharmaceutically acceptable salt, its deuterated analog or combination of pridopidine and at least one of its analog compounds 1-7, or salts thereof for use in treating, reducing the incidence, suppressing, or inhibiting an inflammation induced by viral infection. In some embodiments, the viral infection includes overexpression of pro-inflammatory cytokines, ("cytokine storm").

In some embodiments, the invention provides a composition comprising pridopidine, its pharmaceutically acceptable salt, its deuterated analog or combination of pridopidine and at least one of its analog compounds 1-7, or salts thereof for use in reducing, mitigating or attenuating the expression of interferon stimulated genes.

In some embodiments, this invention provides a composition comprising a selective S1R agonist for use in reducing endoplasmic reticulum stress (ER stress) due to a viral infection, disease or disorder in a subject in need thereof.

In some embodiments, this invention provides a composition comprising a pridopidine, its pharmaceutically acceptable salt, its deuterated analog or combination of pridopidine and at least one of its analog compounds 1-7, or salts thereof for use in reducing endoplasmic reticulum stress (ER stress) due to a viral infection, disease or disorder in a subject in need thereof.

In some embodiment, the composition for use in the methods of this invention comprises pridopidine, or pharmaceutically acceptable salt thereof. In another embodiment, the pridopidine is neutral/free base. In another embodiment, the pridopidine is in its pharmaceutically acceptable salt form.

In another embodiment, the pridopidine salt comprises pridopidine hydrochloride, hydrobromide, hydroiodide, nitrate, sulfate, bisulfate, phosphate, acid phosphate, isonicotinate, acetate, lactate, salicylate, citrate, D,L-tartrate, L-tartarate, D-tartarate, pantothenate, bitartrate, ascorbate, succinate, hemisuccinate, maleate, gentisinate, gentisate, fumarate, gluconate, glucaronate, glycolate, saccharate, formate, besylate, benzoate, glutamate, malate, methanesulfonate, ethanesulfonate, benzensulfonate, p-toluenesulfonate, oxalate, tosylate, naphtalen-2-sulfate, or pamoate (i.e., 1,1'-methylene-bis-(2-hydroxy-3-naphthoate)) salt. In another embodiment, the pridopidine salt is pridopidine hydrochloride.

In an embodiment, the pharmaceutically acceptable salt of pridopidine is pridopidine hydrochloride. In another embodiment, the pharmaceutically acceptable salt of pridopidine is pridopidine hydrobromide. In another embodiment, the pharmaceutically acceptable salt of pridopidine is pridopidine nitrate. In another embodiment, the pharmaceutically acceptable salt of pridopidine is pridopidine perchlorate. In another embodiment, the pharmaceutically acceptable salt of pridopidine is pridopidine phosphate. In another embodiment, the pharmaceutically acceptable salt of pridopidine is pridopidine sulphate. In another embodiment, the pharmaceutically acceptable salt of pridopidine is pridopidine formate. In another embodiment, the pharmaceutically acceptable salt of pridopidine is pridopidine acetate. In another embodiment, the pharmaceutically acceptable salt of pridopidine is pridopidine aconate. In another embodiment, the pharmaceutically acceptable salt of pridopidine is pridopidine ascorbate. In another embodiment, the pharmaceutically acceptable salt of pridopidine is pridopidine benzenesulphonate. In another embodiment, the pharmaceutically acceptable salt of pridopidine is pridopidine benzoate. In another embodiment, the pharmaceutically acceptable salt of pridopidine is pridopidine cinnamate. In another embodiment, the pharmaceutically acceptable salt of pridopidine is pridopidine citrate. In another embodiment, the pharmaceutically acceptable salt of pridopidine is pridopidine embonate. In another embodiment, the pharmaceutically acceptable salt of pridopidine is pridopidine enantate. In another embodiment, the pharmaceutically acceptable salt of pridopidine is pridopidine fumarate. In another embodiment, the pharmaceutically acceptable salt of pridopidine is pridopidine glutamate. In another embodiment, the pharmaceutically acceptable salt of pridopidine is pridopidine glycolate. In another embodiment, the pharmaceutically acceptable salt of pridopidine is pridopidine lactate. In another embodiment, the pharmaceutically acceptable salt of pridopidine is pridopidine maleate. In another embodiment, the pharmaceutically acceptable salt of pridopidine is pridopidine malonate. In another embodiment, the pharmaceutically acceptable salt of pridopidine is pridopidine mandelate. In another embodiment, the pharmaceutically acceptable salt of pridopidine is pridopidine methanesulphonate. In another embodiment, the pharmaceutically acceptable salt of pridopidine is pridopidine naphthalene-2-sulphonate. In another embodiment, the pharmaceutically acceptable salt of pridopidine is pridopidine phthalate. In another embodiment, the pharmaceutically acceptable salt of pridopidine is pridopidine salicylate. In another embodiment, the pharmaceutically acceptable salt of pridopidine is pridopidine sorbate. In another embodiment, the pharmaceutically acceptable salt of pridopidine is pridopidine stearate. In another embodiment, the pharmaceutically acceptable salt of pridopidine is pridopidine succinate. In another embodiment, the pharmaceutically acceptable salt of pridopidine is pridopidine tartrate. In another embodiment, the pharmaceutically acceptable salt of pridopidine is pridopidine toluene-p-sulphonate.

In some embodiment, the composition for use in the method of this invention comprises pridopidine in combination of at least one of its analog compounds 1-7, or salts thereof:

(1)

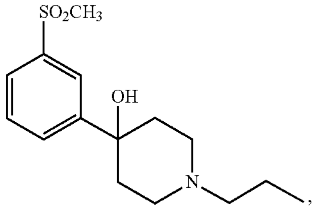
,

-continued (2)

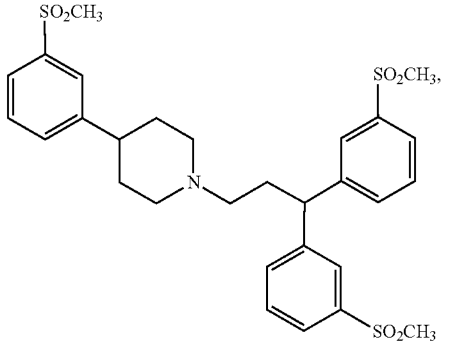

(3)

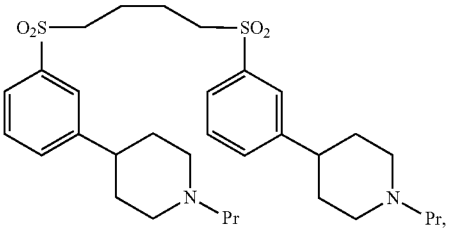

(4)

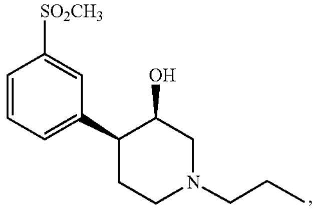

(5)

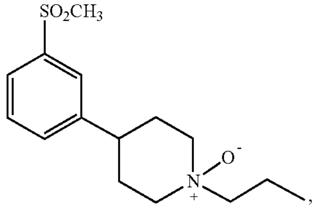

(6)

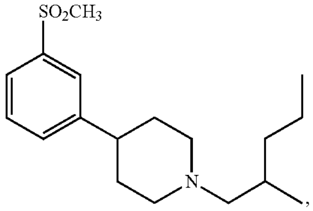

, or (7)

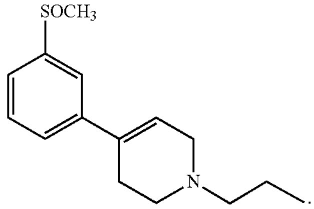

In an embodiment, the pharmaceutically acceptable salt of each of the analog compounds of pridopidine (Compound 1-7) comprises the hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

In other embodiments, the analog compounds 1-7 of pridopidine and their methods of preparation may be found in U.S. Pat. Nos. 10,130,621 and 10,406,145 the entire content of each of which is hereby incorporated by reference.

In some embodiment, the composition for use in the method of this invention comprises pridopidine or pharmaceutically acceptable salt thereof in combination with at least compound 1 or pharmaceutically acceptable salt thereof. In other embodiments, the composition for use in the method of this invention comprises pridopidine or pharmaceutically acceptable salt thereof in combination with compound 4 or pharmaceutically acceptable salt thereof. In other embodiments, the composition for use in the method of this invention comprises pridopidine in combination with compound 1 or pharmaceutically acceptable salt thereof and compound 4 or pharmaceutically acceptable salt thereof. In other embodiments, the composition for use in the method of this invention comprises pridopidine or pharmaceutically acceptable salt thereof in combination with at least compound 2 or pharmaceutically acceptable salt thereof. In other embodiments, the composition for use in the method of this invention comprises pridopidine or pharmaceutically acceptable salt thereof in combination with at least compound 3 or pharmaceutically acceptable salt thereof. In other embodiments, the composition for use in the method of this invention comprises pridopidine or pharmaceutically acceptable salt thereof in combination with at least compound 4 or pharmaceutically acceptable salt thereof. In other embodiments, the composition for use in the method of this invention comprises pridopidine or pharmaceutically acceptable salt thereof in combination with at least compound 5 or pharmaceutically acceptable salt thereof. In other embodiments, the composition for use in the method of this invention comprises pridopidine or pharmaceutically acceptable salt thereof in combination with at least compound 6 or pharmaceutically acceptable salt thereof. In other embodiments, the composition for use in the method of this invention comprises pridopidine or pharmaceutically acceptable salt thereof in combination with at least compound 7 or pharmaceutically acceptable salt thereof. In other embodiments, the weight ratio between pridopidine and at least one of compounds 1-7 is in the range of 1:0.0001 to 1:0.1.

In other embodiments, the weight ratio between pridopidine and at least one of compounds 1-7 is in the range of 1:0.005 to 1:0.1. In other embodiments, the weight ratio between pridopidine and at least one of compounds 1-7 is in the range of 1:0.001 to 1:0.005.

In another embodiment the composition for use in the methods of this invention comprises pridopidine or pharmaceutically acceptable salt thereof in combination with at least one of compounds 1-7, wherein the at least one of compounds 1-7 are in a weight percentage of between 0.01% to 5% of the composition. In another embodiment the composition for use in the methods of this invention comprises pridopidine or pharmaceutically acceptable salt thereof in combination with at least one of compounds 1-7, wherein the at least one of compounds 1-7 are in a weight percentage of between 0.01% to 1%, 0.05 to 0.5% or 0.05% to 1% of the composition. In another embodiment the composition for use in the methods of this invention comprises pridopidine or pharmaceutically acceptable salt thereof in combination with compound 1 or pharmaceutically acceptable salt thereof, wherein compound 1 is in a weight percentage of between 0.01% to 5%, 0.01% to 1%, 0.05 to 0.5% or 0.05% to 1% of the composition. In another embodiment the composition for use in the methods of this invention comprises pridopidine or pharmaceutically acceptable salt thereof in combination with compound 4 or pharmaceutically acceptable salt thereof, wherein compound 4 is in a weight percentage of between 0.01% to 5%, 0.01% to 1%, 0.05 to 0.5% or 0.05% to 1% of the composition.

In another embodiment the composition for use in the methods of this invention comprises pridopidine or pharmaceutically acceptable salt thereof in combination with at least one of compounds 1-7, wherein the at least one of compounds 1-7 are in a weight percentage of between 0.01% to 5% of pridopidine or pharmaceutically acceptable salt. In another embodiment the composition for use in the methods of this invention comprises pridopidine or pharmaceutically acceptable salt thereof in combination with at least one of compounds 1-7, wherein the at least one of compounds 1-7 are in a weight percentage of between 0.01% to 1%, 0.05 to 0.5% or 0.05% to 1% of pridopidine or pharmaceutically acceptable salt. In another embodiment the composition for use in the methods of this invention comprises pridopidine or pharmaceutically acceptable salt thereof in combination with compound 1 or pharmaceutically acceptable salt thereof, wherein compound 1 is in a weight percentage of between 0.01% to 5%, 0.01% to 1%, 0.05 to 0.5% or 0.05% to 1% of pridopidine or pharmaceutically acceptable salt. In another embodiment the composition for use in the methods of this invention comprises pridopidine or pharmaceutically acceptable salt thereof in combination with compound 4 or pharmaceutically acceptable salt thereof, wherein compound 4 is in a weight percentage of between 0.01% to 5%, 0.01% to 1%, 0.05 to 0.5% or 0.05% to 1% of pridopidine or pharmaceutically acceptable salt.

In some embodiments, this invention provides a composition comprising deuterated analog of pridopidine for use in the methods of this invention. "deuterated-analog" refers to "deuterium-enriched" compound that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%. Deuterium-enriched compounds may be obtained by exchanging hydrogen with deuterium or synthesizing the compound with deuterium-enriched starting materials.

In other embodiments, examples of deuterated analogs of pridopidine and their methods of preparation may be found in U.S. Application Publication Nos. 2013-0197031, 2016-0166559 and US-2019-0015401 the entire content of each of which is hereby incorporated by reference.

In other embodiments, a deuterated analog of pridopidine is selected from:

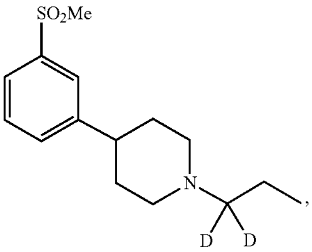

,

-continued

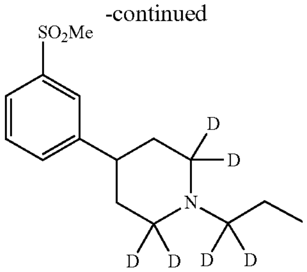

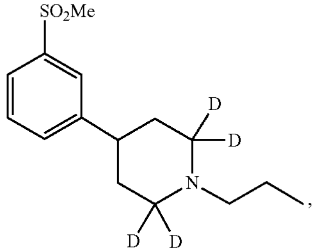

, or

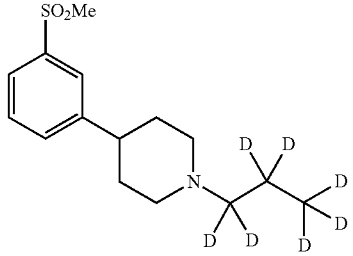

For the methods and use disclosed herein, the route of administration can be, e.g., oral. Routes of administration can also be classified by whether the effect is local (e.g., in topical administration) or systemic (e.g., in enteral or parenteral administration). "Local administration" as used herein shall mean administration of a compound or composition directly to where its action is desired, and specifically excludes systemic administration. "Topical administration" of a compound or composition as used herein shall mean application of the compound or composition to body surfaces such as the skin or mucous membranes such as eyes. "Ocular administration" as used herein shall mean application of a compound or composition to the eye of a subject or to the skin around the eye (periocular skin) or the mucosa around the eye, specifically the conjunctiva of a subject, i.e., local administration.

The amount of pridopidine or the selective S1R agonist and the pharmaceutical compositions of the present invention may be administered by oral administration, topical administration, systemic administration, local administration, or ocular administration.

In some embodiments, the composition disclosed herein for use in the method of this invention is administered via systemic administration. In other embodiments, the composition is administered via oral administration. In other embodiments, the composition is formulated as an oral liquid, solid, semi-solid dosage form, injectable, dermal/transdermal dosage form, ophthalmic dosage forms or as an inhalable composition. In other embodiments, the composition is formulated as an inhalable powder, an injectable, a liquid, a gel, a solid, a capsule, eye drops or as a tablet.

In some embodiments, the composition disclosed herein for use in the method of this invention is administered once daily, twice daily, three times a day or less often than once daily.

In some embodiment, the composition disclosed herein for use in the method of this invention is administered in one dose two doses or three doses per day.

Example of pridopidine derivative is deuterium-enriched version of pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference.

The invention also includes any salt of pridopidine, including any pharmaceutically acceptable salt, wherein pridopidine has a net charge (either positive or negative) and at least one counter ion (having a counter negative or positive charge) is added thereto to form said salt. The phrase "pharmaceutically acceptable salt(s)", as used herein, means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, D,L-tartrate, L-tartarate, D-tartarate, pantothenate, bitartrate, ascorbate, succinate, hemisuccinate, maleate, gentisinate, gentisate, fumarate, gluconate, glucaronate, glycolate, saccharate, formate, besylate, benzoate, glutamate, malate, methanesulfonate, ethanesulfonate, benzensulfonate, p-toluenesulfonate, oxalate, tosylate, naphtalen-2-sulfate, or pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), which is incorporated herein by reference. In another embodiment the pridopidine salt of this invention is a hydrochloride salt.

The present invention thus also relates to pharmaceutical compositions comprising an agent of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrates, lubricants, colorants, flavoring agents, anti-oxidants, and wetting agents.

Pharmaceutical compositions suitable for oral administration may be presented as discrete dosage units such as pills, tablets, dragees or capsules, or as a powder or granules, or as a solution or suspension. The active ingredient may also be presented as a bolus or paste. The compositions can further be processed into a suppository or enema for rectal administration.

The invention further includes a pharmaceutical composition, as herein before described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulizers or insufflators.

The exact dose and regimen of administration of the composition will necessarily be dependent upon the therapeutic or nutritional effect to be achieved and may vary with the formula, the route of administration, and the age and condition of the individual subject to whom the composition is to be administered.

The term "treatment" as used herein refers to the administering of a therapeutic amount of the composition of the present invention which is effective to ameliorate undesired diseases, disorders, including symptoms associated with a diseases or disorders, to prevent the manifestation of such diseases, disorders, including symptoms associated with a diseases or disorders before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above. The "effective amount" for purposes disclosed herein is determined by such considerations as may be known in the art. The amount must be effective to achieve the desired therapeutic effect as described above, depending, inter alia, on the type and severity of the disease to be treated and the treatment regimen. In some embodiment a composition comprising pridopidine or pharmaceutically acceptable salt thereof is between 1-400 mg/day, administered once daily, twice daily, three times per day or less often than once a day. As generally known, an effective amount depends on a variety of factors including the affinity of the ligand to the receptor, its distribution profile within the body, a variety of pharmacological parameters such as half-life in the body, on undesired side effects, if any, on factors such as age and gender, etc.

In some embodiments, pridopidine is administered in a daily dose of between 1 mg/day-400 mg/day. In some embodiments, pridopidine is administered in a daily dose of between 1 mg/day-300 mg/day. In other embodiments, pridopidine is administered in a daily dose of between 1 mg/day-90 mg/day In other embodiments, pridopidine is administered in a daily dose of between 20 mg/day-90 mg/day. In further embodiments, pridopidine is administered in a daily dose of between 45 mg/day-90 mg/day. In other embodiments, pridopidine is administered in a daily dose of between 20 mg/day-50 mg/day. In further embodiments, pridopidine is administered in a daily dose of between 1 mg/day-10 mg/day. In further embodiments, pridopidine is administered in a daily dose of between 10 mg/day-20 mg/day. In further embodiments, pridopidine is administered in a daily dose of between 20 mg/day-30 mg/day. In further embodiments, pridopidine is administered in a daily dose of between 30 mg/day-40 mg/day. In further embodiments, pridopidine is administered in a daily dose of between 40 mg/day-50 mg/day. In further embodiments, pridopidine is administered in a daily dose of between 50 mg/day-60 mg/day. In further embodiments, pridopidine is administered in a daily dose of between 60 mg/day-70 mg/day. In further embodiments, pridopidine is administered in a daily dose of between 70 mg/day-80 mg/day. In further embodiments, pridopidine is administered in a daily dose of between 80 mg/day-90 mg/day. In further embodiments, pridopidine is administered in a daily dose of between 90 mg/day-100 mg/day. In further embodiments, pridopidine is administered in a daily dose of between 100 mg/day-150 mg/day. In further embodiments, pridopidine is administered in a daily dose of between 150 mg/day-200 mg/day. In further embodiments, pridopidine is administered in a daily dose of between 200 mg/day-250 mg/day. In further embodiments, pridopidine is administered in a daily dose of between 250 mg/day-300 mg/day. In further embodiments, pridopidine is administered in a daily dose of between 300 mg/day-350 mg/day. In further embodiments, pridopidine is administered in a daily dose of between 350 mg/day-400 mg/day

EXAMPLES

Example 1: Pridopidine Decreased mHtt-Induced ER Stress

ER-stress was measured in STHdhQ7/7 cells transfected with the mutant Htt96Q-mCherry (expanded, mut-Htt) which showed visible mut Htt-mCherry aggregates. mut Htt-mCherry aggregates appearance were correlated with high levels of accumulated H2a-GFP indicative of ER stress (FIG. 1). STHdhQ7/7 cells expressing Htt20Q-mCherry (wt HTT) or Htt96Q-mCherry (mut HTT) without visible aggregates show low levels of H2a-GFP (no ER stress).

Figure 2:
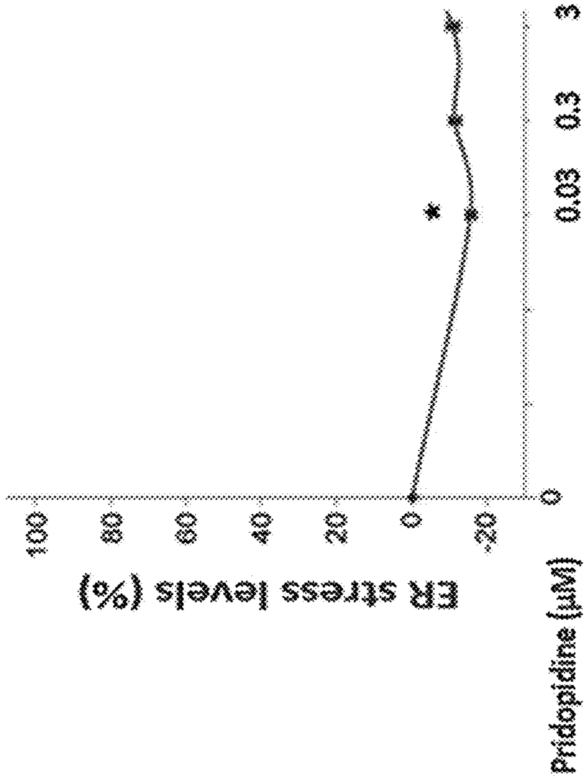
FIG. 2 shows quantification of ER stress in cells with mHTT (left) or WT HTT (right). Pridopidine significantly reduces early mutant Htt-induced ER stress as measured by H2a-GFP aggregation in a dose-dependent manner. For comparative purposes, 100% represents H2a-GFP relative intensity in untreated cells showing mHtt-mCherry aggregates, 0% is H2a-GFP relative intensity in untreated cells without mHtt-mcherry aggregates. The graphs are averages of 3 experiments +-SE. The asterisks indicate P values compared to untreated, <0.05 (*) and <0.01 (**). WT HTT (right) does not induce ER Stress and no effect is observed.
Figure 2:
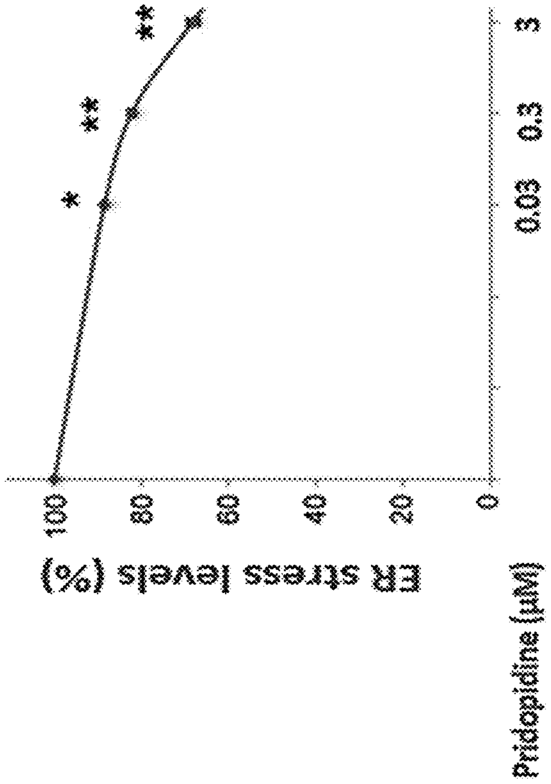

Pridopidine significantly reduced H2a-GFP accumulation in cells positive for mut Htt aggregates in a dose-dependent manner and did not alter H2a-GFP levels in cells without mHTT aggregates or in cells expressing Htt20Q-mCherry (FIG. 2).

Thus, pridopidine decreased Htt-induced ER stress in a dose-dependent manner.

Viral infection-induced ER stress leads to the phosphorylation of eIF2α, which inhibits global translation in the cell, but increases expression of UPR relevant genes, such as ATF4,CHOP, GADD-34, ATF6 and Xbp1 (Bechill et al. 2008; K. Liao et al. 2016).

Example 2: Pridopidine Reduced eIF2α-p Levels

Figure 3:
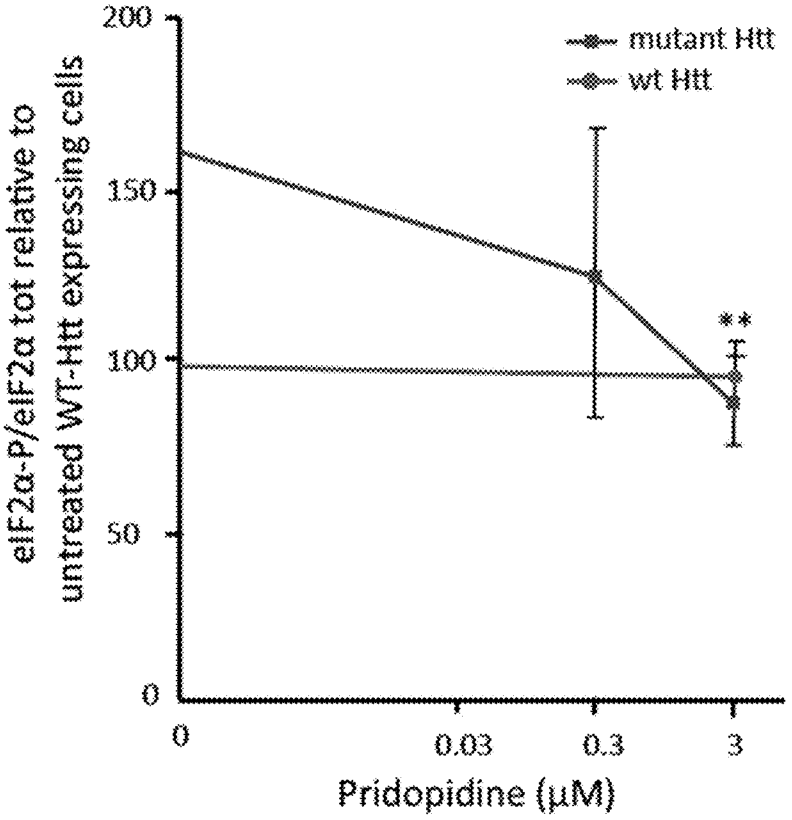
FIG. 3: Pridopidine reduces eIF2α-phosphorylation (ER stress marker) induced by mutant Htt at 8 hours. HEK293 cells were transfected with myc-Htt96Q (mutant HTT, squares) or myc-Htt20Q (wt HTT, circles), then treated with increasing concentrations of pridopidine (from 0.03 to 3 μM) for 8 hours. The ratio of eIF2a-P to total eIF2a was quantified by immunoblot. Pridopidine reduces levels of eIF2a-P in a dose-dependent manner, with a significant effect at the 3 μM dose ($p<0.01$).
Figure 4:
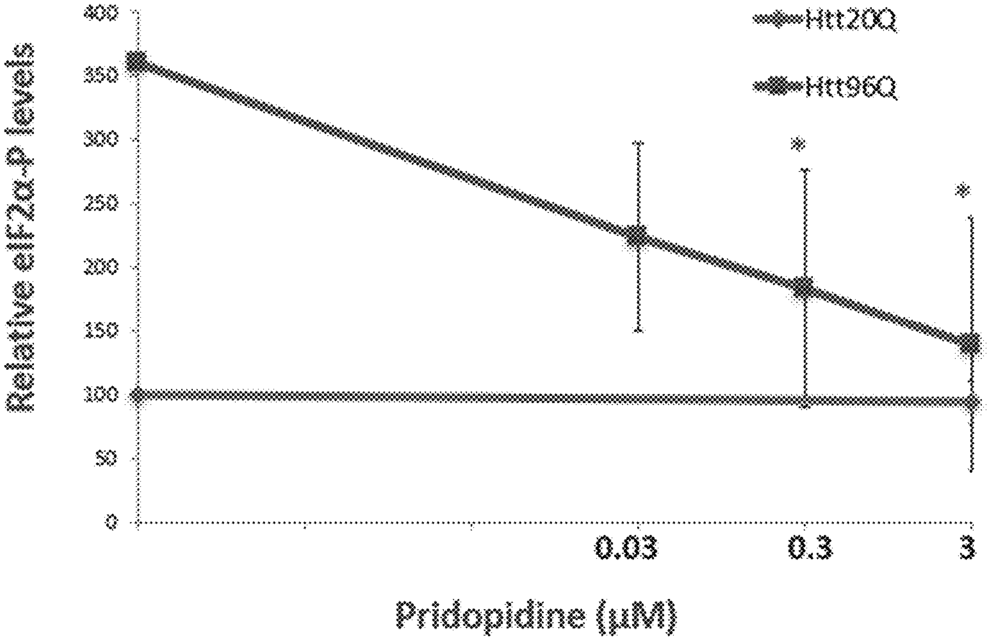
FIG. 4: Pridopidine reduces eIF2α-phosphorylation (ER stress marker)) induced by mutant Htt at 24 hours. HEK293 cells were transfected with myc-Htt96Q (mutant HTT, squares) or myc-Htt20Q (wt HTT, circles), then treated with increasing concentrations of pridopidine (from 0.03 to 3 μM) for 24 hours. The ratio of eIF2a-P to total eIF2a was quantified by immunoblot. Pridopidine reduces levels of eIF2a-P in a dose-dependent manner with a significant effect at the 0.3 and 3 μM concentrations ($p<0.05$).

The effect of pridopidine on ER stress was studied by assessing phosphorylation levels of the translation initiation factor eIF2α. Phosphorylation of eIF2α is a hallmark of the ER stress response. In FIGS. 3 and 4, HEK293 cells expressing the mutant Htt protein (Htt96Q) show a 1.7- and a 3.5-fold increase, respectively, in eIF2α-phosphorylation (eIF2α-p) compared to cells expressing WT Htt (Htt20Q). Pridopidine treatment caused a significant dose-dependent reduction in eIF2α-phosphorylation (ratio of eIF2α-P/eIF2α) at both 8 hours (FIG. 3) and 24 hours (FIG. 4) indicating a reduction in cellular ER stress.

Figure 5:
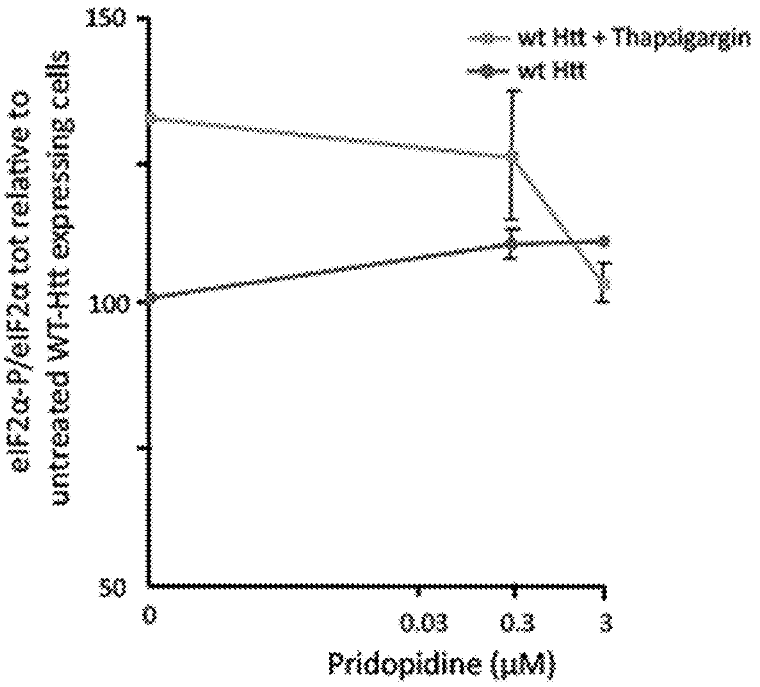
FIG. 5: Pridopidine reduces eIF2α-phosphorylation (ER stress marker) in cells in which ER stress is induced by thapsigargin. Thapsigargin is a potent inducer of ER stress. HEK293 cells transfected with myc-Htt20Q (wt HTT) were treated or not with 2 μg/ml thapsigargin, which causes a 70% increase in phosphorylated eIF2α (eIF2α-p). Pridopidine treatment reduces p-eIF2α levels (3 μM).

The effect of pridopidine on ER stress was also evaluated in cells in which ER stress was not induced by mutant huntingtin, but by the potent ER-stress inducer thapsigargin. HEK293 cells transfected with Htt20Q-mCherry (wt HTT) were treated with 2 μg/ml thapsigargin to induce ER stress. Pridopidine (3 μM) treatment caused a reduction in eIF2α-p (ratio of eIF2α-P/eIF2α) after 8 hours of treatment (FIG. 5), indicating that pridopidine reduces ER stress regardless of the underlying cause.

Figure 6:
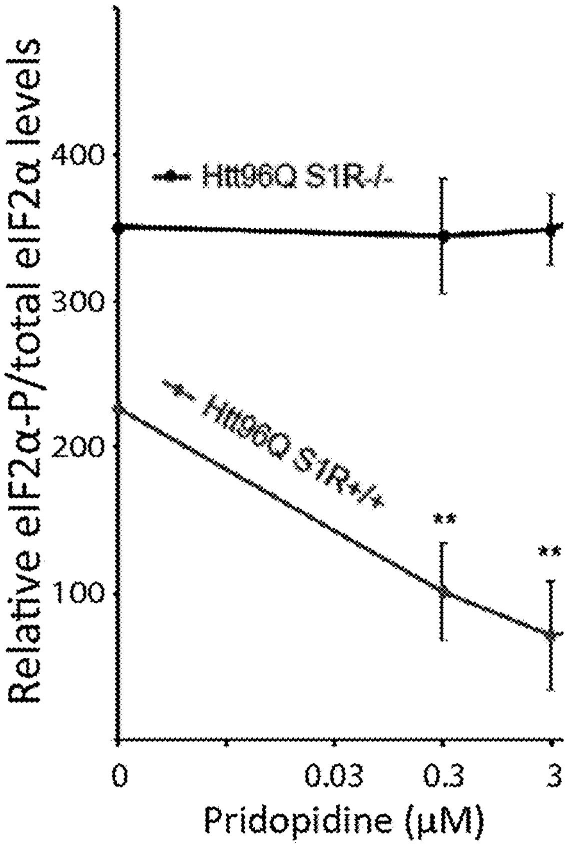
FIG. 6: Pridopidine reduces eIF2α-phosphorylation (ER stress marker) in a S1R-dependent mechanism. HEK293 cells were transfected with a guide RNA(gRNA) targeting human S1R or a control gRNA. Htt96Q (mHTT) was transiently expressed in HEK 293 cells. Cells were treated with 0.3 and 3 μM pridopidine for 8 h. The ratio of eIF2α-P to total eIF2α was measured by immunoblotting and quantified. Pridopidine treatment reduces p-eIF2α levels at the 0.3 and 3 μM concentrations ($p<0.01$) in cells expressing the S1R (S1R+/+). However, this effect is abolished in the absence of S1R (S1R−/− cells) indicating that the ER-stress reducing effect of pridopidine in mediated by the S1R. Data is mean±SD of 3 experiments.

Example 3: Pridopidine Reduced eIF2α-p (ER Stress) in a SIR-Dependent Mechanism To evaluate whether the effect of pridopidine on ER stress is S1R-mediated, eIF2α-phosphorylation levels were assessed in HEK293 cells in which the S1R was genetically deleted using CRISPR/Cas9 (S1R−/−). ER stress was induced by transfection of mutant Htt (Htt96Q). In S1R+/+ cells, Htt96Q increased ER stress as measured by a two-fold increase in eIF2α-P levels. Pridopidine treatment (0.3 and 3 μM) significantly reduced eIF2α-P levels (FIG. 6). The genetic deletion of S1R (S1R−/−) also contributes to the increase in eIF2α-P levels indicating the involvement of the S1R in mediating ER stress levels. Pridopidine treatment of S1R−/− cells transfected with Htt96Q had no effect on eIF2α-P levels indicating the effect of pridopidine is mediated exquisitely via the SIR.

Levels of the UPR pathway proteins ATF4, CHOP, GADD-34, ATF6 and Xbp1 were upregulated in multiple cellular models in response to their infection by coronaviruses (i.e. Infectious Bronchitis Virus (IBV) and mouse hepatitis virus (MEW)) (Y. Liao et al. 2013; Bechill et al. 2008). Bioinformatics analysis predicts similar effects by SARS-CoV2 (Nabirotchkin et al. 2020).

Example 4: Pridopidine Reduced Levels of UPR PERK Pathway Markers

Figure 7A:
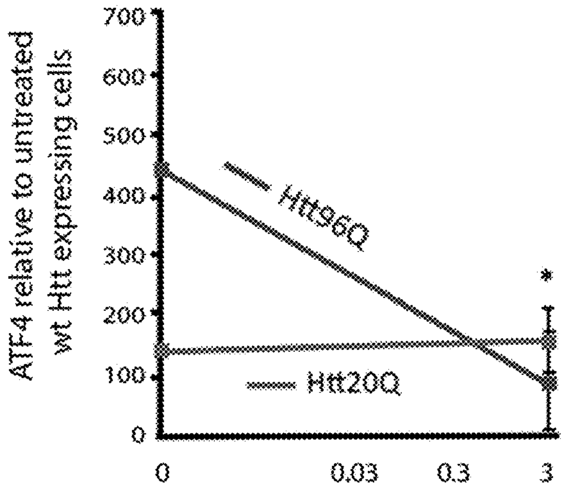
FIGS. 7A-7C: Pridopidine reduces protein levels of the unfolded response pathway (UPR) markers ATF4 (FIG. 7A), CHOP (FIG. 7B) and GADD34 (FIG. 7C). Cells expressing myc-Htt96Q (mutant Htt) or myc-Htt20Q (wt Htt) were treated with pridopidine 3 uM. Immunoblots were reacted with anti-ATF4 (FIG. 7A), anti-CHOP (FIG. 7B) and anti-GADD34 (FIG. 7C), quantified and normalized with anti-actin or anti-tubulin as loading controls. Pridopidine (3 μM) reduces ATF4 levels by ~4.5-fold ($p<0.05$), CHOP by ~2-fold, and GADD-34 by ~2.5-fold ($p<0.01$).
Figure 7B:
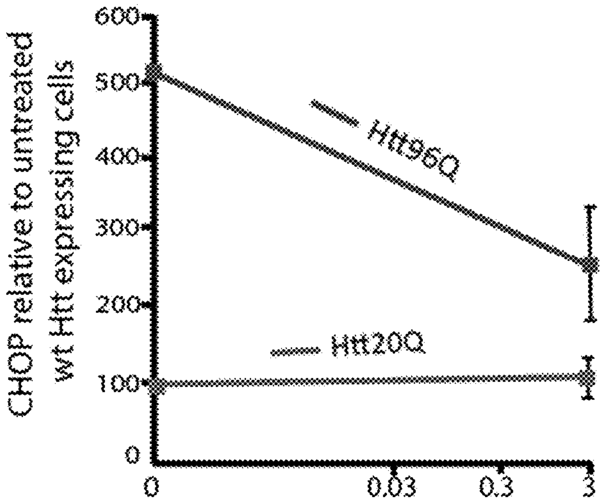
Figure 7C:
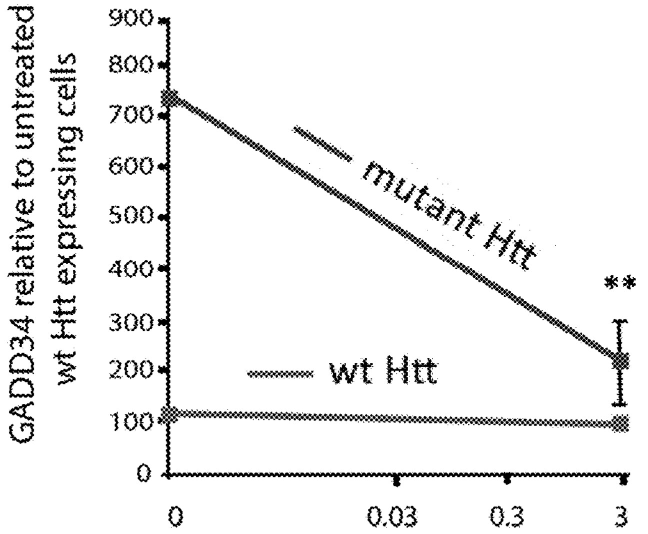

ATF4 translation was increased in response to ER-stress and eIF2α phosphorylation, and is part of the UPR pathway, initiating a cascade of transcriptional responses including increased CHOP and GADD-34 translation. The effect of pridopidine on ATF4, CHOP and GADD-34 protein levels was assessed in HEK293 in which ER stress was induced by mutant Htt (Htt96Q). Htt96Q-induced ER stress increases ATF4 levels 4.5-fold (FIG. 7A), CHOP levels 5-fold (FIG. 7B), and GADD-34 levels 7-fold (FIG. 7C) compared to cells transfected with wt Htt (Htt20Q). Pridopidine treatment reduces ATF4, CHOP and GADD-34 to normal wt levels.

Figure 8:
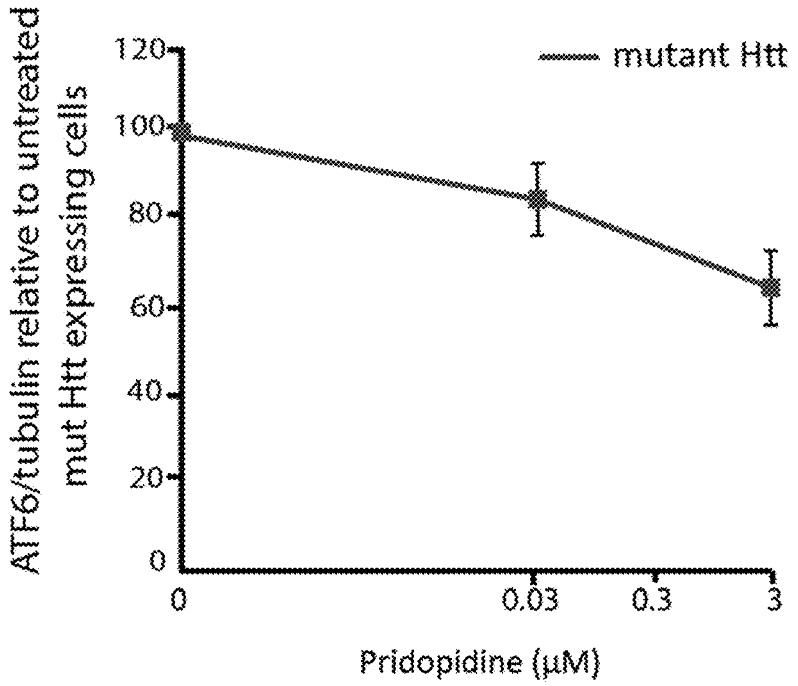
FIG. 8: Pridopidine reduces protein levels of the UPR marker ATF6. Cells expressing myc-Htt96Q (mutant Htt) were treated with pridopidine 0.03 and 3 μM. Immunoblots were reacted with anti-ATF6 quantified and normalized with anti-tubulin as loading controls. Pridopidine at both concentrations reduces ATF6 by ~10% and ~30% at the 0.03 and 3 μM concentrations, respectively.
Figure 9:
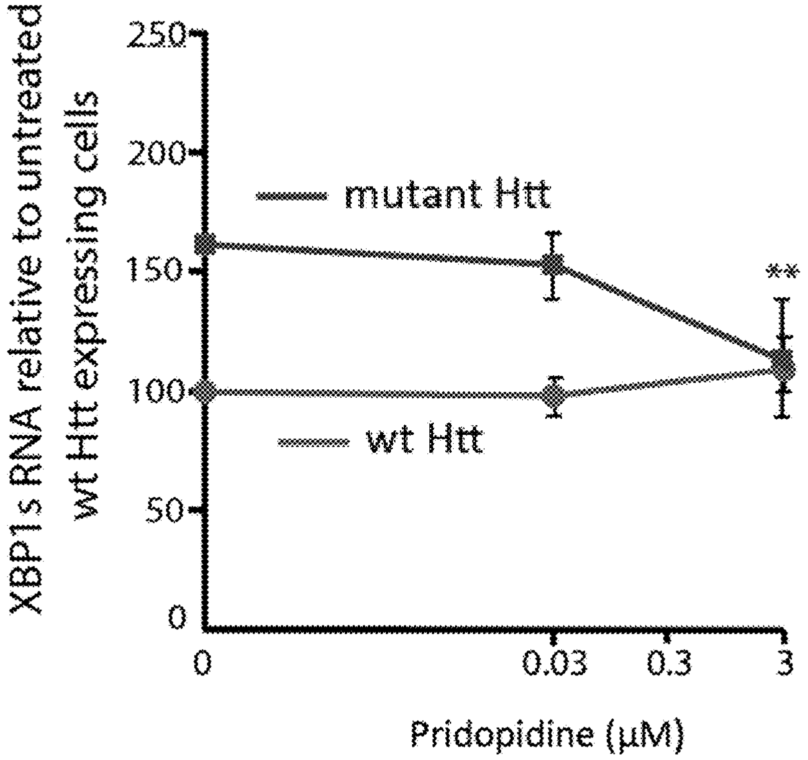
FIG. 9: Pridopidine reduces mRNA levels of the UPR marker XBP1s. Cells expressing myc-Htt96Q (mutant Htt) or myc-Htt20Q (wt Htt) were treated with pridopidine 0.03 and 3 μM. XBP1s RNA levels were determined by quantitative PCR (polymerase chain reaction). Xbp1s levels are increased by 70% in mutant Htt transfected cells. Pridopidine treatment demonstrates a significant 25% reduction in XBP1s levels at the 3 μM concentration ($p<0.01$).

Example 5: Pridopidine Reduced Levels of UPR Pathway Arms ATF6 and IRE Markers ER stress was evident in HD cells as measured by the increase of two additional UPR pathways: the ATF6 pathway and the IRE1 pathway, (increase in Xbp1 splicing). In HEK293 cells, ATF6 levels were undetectable in Htt20Q-transfected cells and were therefore increased in mutant Htt96Q-transfected cells. Pridopidine treatment (3 μM) reduced ATF6 levels by 35% (FIG. 8). In the IRE1 arm of the UPR pathway, mRNA levels of Xbp1s were increased by ~60%. Pridopidine treatment (3 μM) significantly reduced Xbp1s mRNA levels by 25% (FIG. 9). These data indicate that pridopidine reduces the activation of all three arms of the ER-stress induced UPR pathway.

Example 6: Pridopidine Reduced Mitochondrial ROS Production

Figure 10:
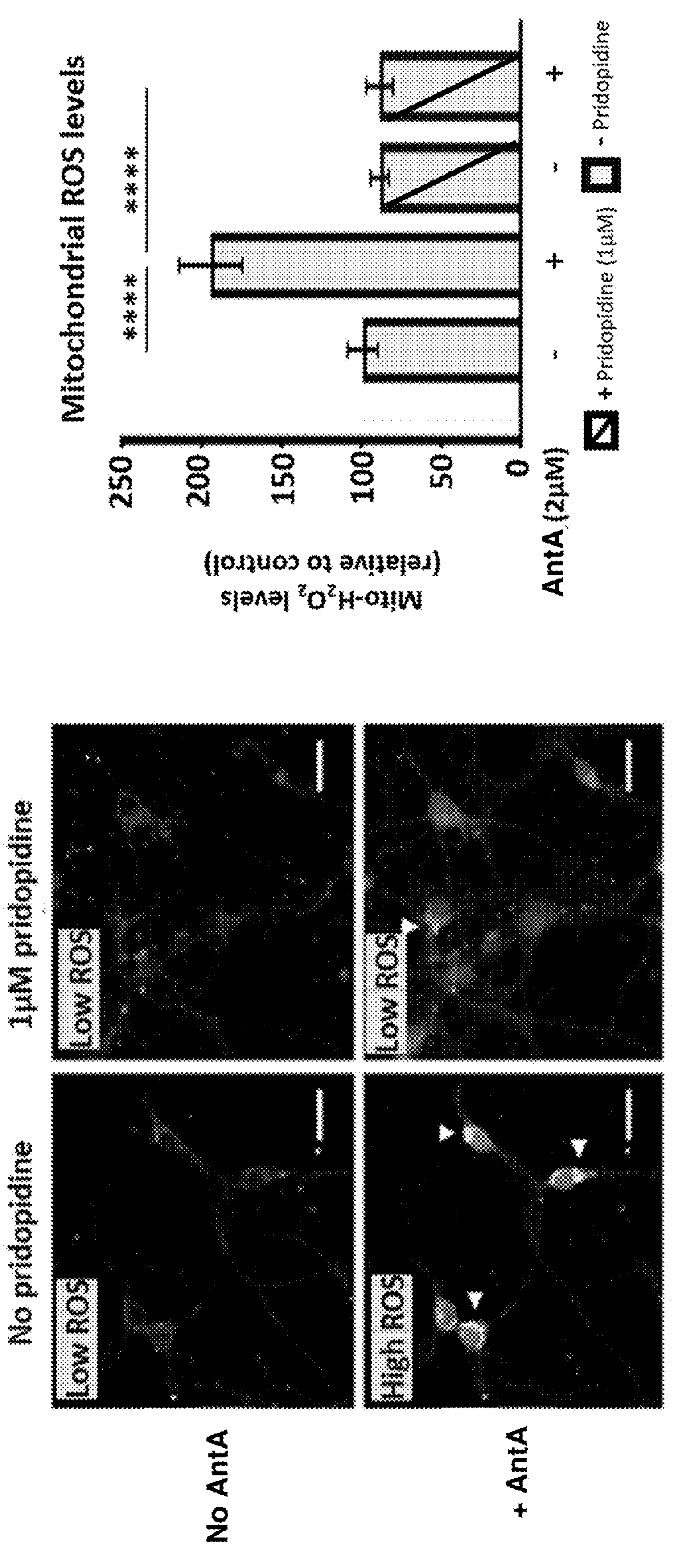
FIG. 10: Pridopidine reduces mitochondrial Reactive Oxidative Species (ROS) in YAC128 HD striatal neurons. YAC128 is a mouse model of Huntington's Disease (HD), Striatal neurons from wt or YAC128 were treated or not with 1 μM pridopidine and incubated with MitoPY1 fluorescence probe. The mitochondrial respiration inhibitor Antimycin A (Ant A, 2 μM) was used to induce release of Mitochondrial $H_2O_2$ and oxidative stress. Mitochondrial $H_2O_2$ was recorded in spinning disk confocal before and after administration of Ant A (n=4, considering ~20 cells/condition). Ant A increases $H_2O_2$ in untreated cells ~2-fold. Pridopidine treatment inhibits $H_2O_2$ release and oxidative stress. Scale bar=30 μM. Two-way ANOVA reveals a rescuing effect of pridopidine treatment on mitochondrial ROS production [F(1,389=15.24; $p<0.0001$].

HD mouse neurons showed increased susceptibility to oxidative challenges, resulting in increased levels of reactive oxygen species (ROS) and a deficient antioxidant response. Striatal neurons from YAC128 HD mice were treated with 1 μM pridopidine prior to induction of ROS production by the mitochondrial respiration inhibitor antimycin A (Ant A). Ant A increased ROS production ~2-fold in the YAC128 neurons. Pridopidine (1 μM) showed robust and significant reduction of ROS production by mitochondria back to normal levels (FIG. 10).

ATF4 and CHOP are involved in the regulation of mitochondrial function (Šileikytė and Forte 2019). By affecting ATF4 and CHOP levels, as suggested by bioinformatic analysis (Nabirotchkin et al. 2020), SARS-CoV2 can disrupt this regulation to avoid apoptosis, similarly to previously described coronaviruses which have been shown to interfere with mitochondrial function (Kim et al. 2018).

Example 7: SARS-CoV-2 Infection Reduces Mitochondrial Membrane Potential

The Nsp10 protein of SARS-CoV directly interacts with cytochrome oxidase II, a component of mitochondrial complex IV. This interaction leads to a decrease in the activity of cytochrome oxidase, and to a loss of inner mitochondrial membrane potential. Taken together, SARS-CoV-2 impacts the oxido-reductase system of the mitochondria and reduces mitochondrial membrane potential (Q. Li et al. 2005).

Example 8: Pridopidine Increases Mitochondrial Membrane Potential

Figure 11:
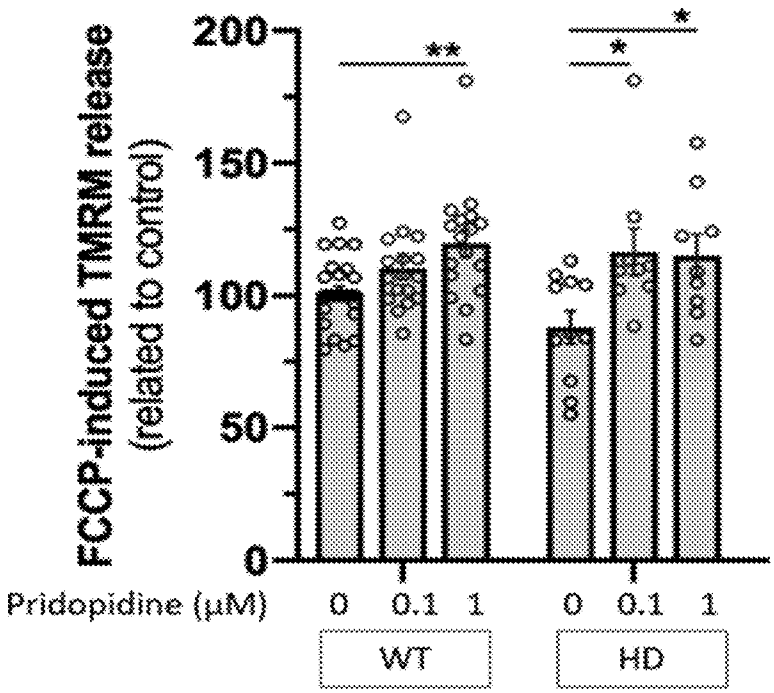
FIG. 11: Pridopidine increases mitochondrial membrane potential (MMP) in cortical HD neurons after oxidative stress. Striatal WT and YAC128 (HD) neurons were treated with pridopidine for 24 h and TMRM (Tetramethylrhodamine methyl Ester) was used to evaluate changes in MMP after depolarization with oligomycin plus FCCP (Carbonylcyanide-4-phenylhydrazone) (n=7-10). HD neurons show reduced MMP. Pridopidine treatment enhances MMP in wt neurons and significantly restores the impaired MMP in HD neurons (2-way ANOVA analysis [$F(2,107)=3.257$; $p=0.0423$].

The role of S1R in regulating mitochondrial membrane potential (MMP) was studied in striatal neurons from wild-type (WT) control and YAC128 HD mice. HD neurons show reduced MMP compared to WT. In WT neurons, pridopidine causes a significant increase in MMP at 1 μM, and a trend towards increasing MMP at 0.1 μM. In HD neurons, in which MMP is reduced by 25% compared to WT, pridopidine at both doses caused a significant increase in MMP. Thus, pridopidine rescues the impaired membrane potential (FIG. 11).

Figure 12:
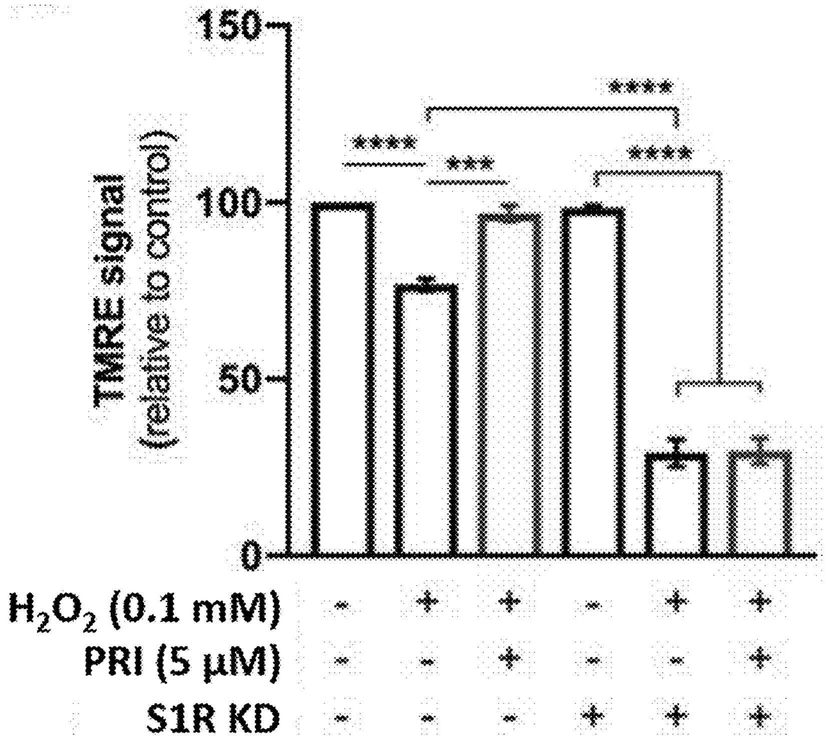
FIG. 12: The effect of pridopidine on mitochondrial membrane potential (MMP) is mediated by the S1R. The S1R was genetically knocked down (KD) in lymphoblasts from HD patients (S1R KD), showing a decrease of ~83% in S1R protein levels. Cells were treated with pridopidine 5 μM, then challenged with 0.1 mM $H_2O_2$. MMP was quantified by TMRE (Tetramethylrhodamine ethyl ester) signal in control and S1R-KD HD lymphoblasts (5 μM, 24 h, n=4). $H_2O_2$ treatment significantly reduced MMP in both S1R+/+ and S1R KD cells, by 25% and 75%, respectively. Pridopidine treatment completely restored MMP in S1R+/+ cells, but not in S1R KD cells, indicating that the effect of pridopidine is mediated via the S1R. ****$p<0.0001$ by Kruskal Wallis test followed by Dunn multiple comparison test.

Example 9: Pridopidine Effects on Mitochondrial Membrane Potential are Mediated by the S1R To confirm that the effects of pridopidine are mediated by the S1R, the S1R was knocked down in HD lymphoblasts, achieving approximately 83% reduction in protein levels. $H_2O_2$ treatment significantly reduced MMP in both S1R+/+ and S1R-KD cells, by 25% and 75%, respectively. Pridopidine treatment (5 μM) completely restored MMP in S1R+/+ cells, but not in S1R KD cells. Thus, pridopidine has a protective effect on MMP. The effect of pridopidine on $H_2O_2$ challenge-induced MMP reduction was abolished in cells with reduced S1R levels ($p<0.001$), indicating that pridopidine effects are S1R-dependent (FIG. 12).

Example 10: Pridopidine Reduces the Expression of Inflammatory Genes Induced by Viral Infection A viral infection induces expression of pro-inflammatory cytokines (such as interferon, IFN) and the induction of IFN Stimulated Genes (ISGs). The ISGs are a wide array of genes that initially function together to inhibit viral replication. However, prolonged expression of ISGs can have detrimental effects.

Continued viral infection and overexpression of cytokines is referred to as a "cytokine storm" which is associated with prolonged upregulation of ISGs. A cytokine storm and prolonged ISGs upregulation result in enhanced inflammation, persistent viral infection and promotion of the disease.

The body's ability to control the inflammatory response, including attenuation of the cytokine storm, is key to its healing and survival post-infection. Reducing the expression of ISGs can attenuate cytokine levels and reduce inflammation.

Figure 13:
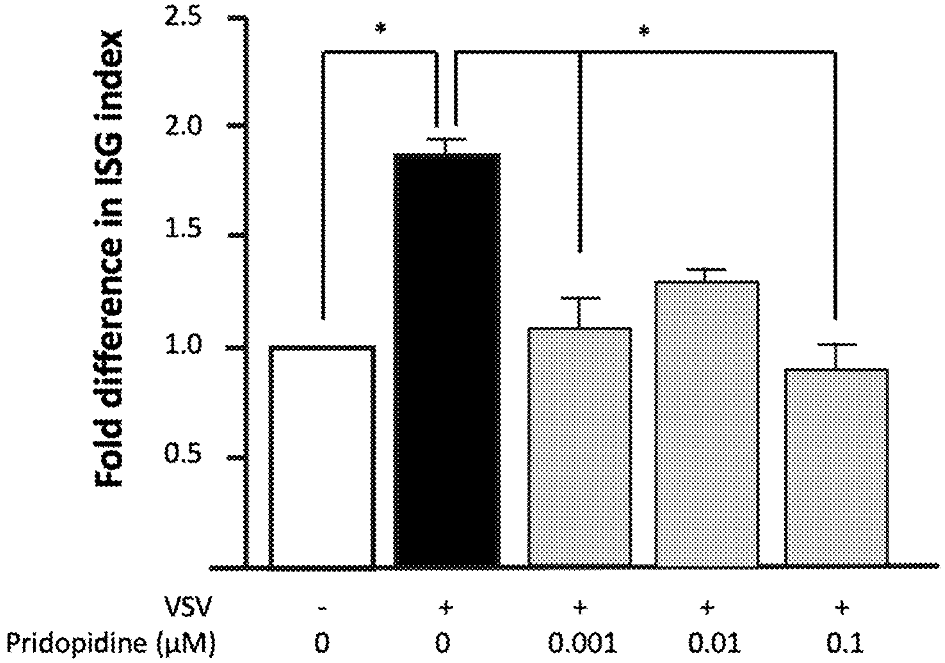
FIG. 13: Pridopidine mitigates viral-induced inflammatory gene expression. HEK293 cells were pre-treated with pridopidine and infected with the model virus Vesicular Stomatitis Virus (VSV). Gene expression levels of the interferon-stimulated genes (ISGs) Interferon-Induced Protein With Tetratricopeptide Repeats 1 (IFIT1), Eukaryotic Translation Initiation Factor 2 Alpha Kinase 2 (EIF2AKS) and Interferon Regulatory Factor 7 (IRF7) were analyzed by qualitative reverse transcriptase polymerase chain reaction (qRT-PCR). Expression levels were first normalized to the housekeeping gene GAPDH, then to the expression levels in control, uninfected cells (defined as 1, white bar). Data is mean±SEM. *$p<0.05$, one-sided Student's t-test.

Viral infection by the model virus Vesicular Stomatitis Virus (VSV) induced an inflammatory response and significantly upregulated the expression of the ISGs Interferon-Induced Protein With Tetratricopeptide Repeats 1 (IFIT1), Eukaryotic Translation Initiation Factor 2 Alpha Kinase 2 (EIF2AK2) and Interferon Regulatory Factor 7 (IRF7) in HEK293 cells (FIG. 13, black bar).

The effect of pridopidine on these ISGs was evaluated in HEK293 cells infected with VSV. In this study, the ISGs were compiled together to create an ISG index. A high expression of the ISG index indicates strong inflammatory and toxic cytokine storm due to viral infection.

Treatment with pridopidine reduced the expression of these ISGs (indexed together) by ~30-50% at concentrations of 0.001, 001 and 0.1 Thus, pridopidine showed an anti-inflammatory beneficial effect measured by down-regulation of ISGs.

REFERENCES CITED IN THIS APPLICATION

Allahtavakoli, Mohammad, and Bevyn Jarrott. 2011. "Sigma-1 Receptor Ligand PRE-084 Reduced Infarct Volume, Neurological Deficits, pro-Inflammatory Cytokines and Enhanced Anti-Inflammatory Cytokines after Embolic Stroke in Rats." *Brain Research Bulletin*. https://doi.org/10.1016/j.brainresbull.2011.03.019.

Alon, Assaf, Hayden R. Schmidt, Michael D. Wood, James J. Sahn, Stephen F. Martin, and Andrew C. Kruse. 2017. "Identification of the Gene That Codes for the Σ2 Receptor." *Proceedings of the National Academy of Sciences of the United States of America*. https://doi.org/10.1073/pnas.1705154114.

Bechill, John, Zhongbin Chen, Joseph W. Brewer, and Susan C. Baker. 2008. "Coronavirus Infection Modulates the Unfolded Protein Response and Mediates Sustained Translational Repression." *Journal of Virology*. https://doi.org/10.1128/jvi.00017-08.

Cava, Claudia, Gloria Bertoli, and Isabella Castiglioni. 2020. "In Silico Discovery of Candidate Drugs against Covid-19." *Viruses*. https://doi.org/10.3390/v12040404.

Chan, Ching-Ping, Kam-Leung Siu, King-Tung Chin, Kwok-Yung Yuen, Bojian Zheng, and Dong-Yan Jin. 2006. "Modulation of the Unfolded Protein Response by the Severe Acute Respiratory Syndrome Coronavirus Spike Protein." *Journal of Virology*. https://doi.org/10.1128/jvi.00659-06.

Chen, Chia-Yen, Yueh-Hsin Ping, Hsin-Chen Lee, Kuan-Hsuan Chen, Yuan-Ming Lee, Yu-Juin Chan, Te-Cheng Lien, et al. 2007. "Open Reading Frame 8a of the Human Severe Acute Respiratory Syndrome Coronavirus Not Only Promotes Viral Replication but Also Induces Apoptosis." *The Journal of Infectious Diseases*. https://doi.org/10.1086/519166.

Christ, Maximilian, Heike Huesmann, Heike Nagel, Andreas Kern, and Christian Behl. 2019. "Sigma-1 Receptor Activation Induces Autophagy and Increases Proteostasis Capacity In Vitro and In Vivo." *Cells*. https://doi.org/10.3390/cells8030211.

DeDiego, Marta L., Jose L. Nieto-Torres, Jose M. Jiménez-Guardeño, Jose A. Regla-Nava, Enrique Álvarez, Juan Carlos Oliveros, Jincun Zhao, Craig Fett, Stanley Perlman, and Luis Enjuanes. 2011. "Severe Acute Respiratory Syndrome Coronavirus Envelope Protein Regulates Cell Stress Response and Apoptosis." *PLoS Pathogens*. https://doi.org/10.1371/journal.ppat.1002315.

Delprat, Benjamin, Lucie Crouzier, Tsung Ping Su, and Tangui Maurice. 2020. "At the Crossing of ER Stress and MAMs: A Key Role of Sigma-1 Receptor?" In *Advances in Experimental Medicine and Biology*. https://doi.org/10.1007/978-3-030-12457-1_28.

Fung, To S., and Ding X. Liu. 2014. "Coronavirus Infection, ER Stress, Apoptosis and Innate Immunity." *Frontiers in Microbiology*. https://doi.org/10.3389/fmicb.2014.00296.

Gassen, Nils C., Daniela Niemeyer, Doreen Muth, Victor M. Corman, Silvia Martinelli, Alwine Gassen, Kathrin Hafner, et al. 2019. "SKP2 Attenuates Autophagy through Beclin1-Ubiquitination and Its Inhibition Reduces MERS-Coronavirus Infection." *Nature Communications*. https://doi.org/10.1038/s41467-019-13659-4.

Gordon, David E, Gwendolyn M Jang, Mehdi Bouhaddou, Jiewei Xu, Kirsten Obernier, Matthew J O' Meara, Jeffrey Z Guo, et al. 2020. "A SARS-CoV-2-Human Protein-Protein Interaction Map Reveals Drug Targets and Potential Drug-Repurposing." *BioRxiv*. https://doi.org/10.1101/2020.03.22.002386.

Harapan, Harapan, Naoya Itoh, Amanda Yufika, Wira Winardi, Synat Keam, Heyhpeng Te, Dewi Megawati, Zinatul Hayati, Abram L. Wagner, and Mudatsir Mudatsir. 2020. "Coronavirus Disease 2019 (COVID-19): A Literature Review." *Journal of Infection and Public Health*. https://doi.org/10.1016/j.jiph.2020.03.019.

Johnston, Tom H., Michal Geva, Lilach Steiner, Aric Orbach, Spyros Papapetropoulos, Juha Matti Savola, Ian J. Reynolds, et al. 2019. "Pridopidine, a Clinic-Ready Compound, Reduces 3,4-Dihydroxyphenylalanine-Induced Dyskinesia in Parkinsonian Macaques." *Movement Disorders* 34 (5): 708-16. https://doi.org/10.1002/mds.27565.

Katnik, C., Y. Herrera, K. R. Pennypacker, J. Cuevas, and W. R. Guerrero. 2006. "Sigma-1 Receptor Activation Prevents Intracellular Calcium Dysregulation in Cortical Neurons during in Vitro Ischemia." *Journal of Pharmacology and Experimental Therapeutics* 319 (3): 1355-65. https://doi.org/10.1124/jpet.106.107557.

Kim, Seong Jun, Dae Gyun Ahn, Gulam H. Syed, and Aleem Siddiqui. 2018. "The Essential Role of Mitochondrial Dynamics in Antiviral Immunity." *Mitochondrion. https://doi.org/*10.1016/j.mito.2017.11.007.

Li, Qihan, Lichun Wang, Chenghong Dong, Yanchun Che, Li Jiang, Longding Liu, Hongling Zhao, et al. 2005. "The Interaction of the SARS Coronavirus Non-Structural Protein 10 with the Cellular Oxido-Reductase System Causes an Extensive Cytopathic Effect." *Journal of Clinical Virology*. https://doi.org/10.1016/j.jcv.2004.12.019.

Li, Shumin, Lixia Yuan, Guo Dai, Rui Ai Chen, Ding Xiang Liu, and To Sing Fung. 2020. "Regulation of the ER Stress Response by the Ion Channel Activity of the Infectious Bronchitis Coronavirus Envelope Protein Modulates Virion Release, Apoptosis, Viral Fitness, and Pathogenesis." *Frontiers in Microbiology*. https://doi.org/10.3389/fmicb.2019.03022.

Liao, Ke, Minglei Guo, Fang Niu, Lu Yang, Shannon E Callen, and Shilpa Buch. 2016. "Cocaine-Mediated Induction of Microglial Activation Involves the ER Stress-TLR2 Axis." *Journal of Neuroinflammation*, 1-16. https://doi.org/10.1186/s12974-016-0501-2.

Liao, Y., T. S. Fung, M. Huang, S. G. Fang, Y. Zhong, and D. X. Liu. 2013. "Upregulation of CHOP/GADD153 during Coronavirus Infectious Bronchitis Virus Infection Modulates Apoptosis by Restricting Activation of the Extracellular Signal-Regulated Kinase Pathway." *Journal of Virology*. https://doi.org/10.1128/jvi.00626-13.

Longhitano, Lucia, Carlo Castruccio Castracani, Daniele Tibullo, Roberto Avola, Maria Viola, Giuliano Russo, Orazio Prezzavento, et al. 2017. "Sigma-1 and Sigma-2 Receptor Ligands Induce Apoptosis and Autophagy but Have Opposite Effect on Cell Proliferation in Uveal Melanoma." *Oncotarget*. https://doi.org/10.18632/oncotarget.19556.

Maurice, Tangui, Masayuki Hiramatsu, Jiro Itoh, Tsutomu Kameyama, Takaaki Hasegawa, and Toshitaka Nabeshima. 1994. "Behavioral Evidence for a Modulating Role of σ Ligands in Memory Processes. I. Attenuation of Dizocilpine (MK-801)-Induced Amnesia." *Brain Research* 647 (1): 44-56. https://doi.org/10.1016/0006-8993(94)91397-8.

Nabirotchkin, Serguei, Alex E Peluffo, Jan Bouaziz, and Daniel Cohen. 2020. "Focusing on the Unfolded Protein Response and Autophagy Related Pathways to Reposition Common Approved Drugs against COVID-19." *Preprints*. https://doi.org/10.20944/preprints202003.0302.v1.

Ricardo J Jose, and Ari Manuel. 2020. "COVID-19 Cytokine Storm: The Interplay between Inflammation and Coagulation." *The Lancet Respiratory Medicine*.

Šileikytė, Justina, and Michael Forte. 2019. "The Mitochondrial Permeability Transition in Mitochondrial Disorders." *Oxidative Medicine and Cellular Longevity*. https://doi.org/10.1155/2019/3403075.

Starkov, Anatoly A. 2008. "The Role of Mitochondria in Reactive Oxygen Species Metabolism and Signaling." In *Annals of the New York Academy of Sciences*. https://doi.org/10.1196/annals.1427.015.

Tesei, Anna, Michela Cortesi, Sara Pignatta, Chiara Arienti, Giulio Massimo Dondio, Chiara Bigogno, Alessio Malacrida, et al. 2019. "Anti-Tumor Efficacy Assessment of the Sigma Receptor Pan Modulator RC-106. A Promising Therapeutic Tool for Pancreatic Cancer." *Frontiers in Pharmacology*. https://doi.org/10.3389/fphar.2019.00490.

Tesei, Anna, Michela Cortesi, Alice Zamagni, Chiara Arienti, Sara Pignatta, Michele Zanoni, Mayra Paolillo, et al. 2018. "Sigma Receptors as Endoplasmic Reticulum Stress 'Gatekeepers' and Their Modulators as Emerging New Weapons in the Fight against Cancer." *Frontiers in Pharmacology*. https://doi.org/10.3389/fphar.2018.00711.

Wang, Jing-Zhang, Rui-Ying Zhang, and Jing Bai. 2020. "An Anti-Oxidative Therapy for Ameliorating Cardiac Injuries of Critically Ill COVID-19-Infected Patients." *International Journal of Cardiology*. https://doi.org/10.1016/j.ijcard.2020.04.009.

Weng, Tzu Yu, Shang Yi Anne Tsai, and Tsung Ping Su. 2017. "Roles of Sigma-1 Receptors on Mitochondrial Functions Relevant to Neurodegenerative Diseases." *Journal of Biomedical Science* 24 (1): 1-14. https://doi.org/10.1186/s12929-017-0380-6.

Zhao, Jing, Yonju Ha, Gregory I. Liou, Graydon B. Gonsalvez, Sylvia B. Smith, and Kathryn E. Bollinger. 2014. "Sigma Receptor Ligand, (+)-Pentazocine, Suppresses Inflammatory Responses of Retinal Microglia." *Investigative Ophthalmology and Visual Science*. https://doi.org/10.1167/iovs.13-12823.

What is claimed is:

1. A method for treating, reducing the incidence, suppressing or inhibiting a viral infection, disease, disorder or symptoms thereof in a subject in need thereof comprising administering to the subject a composition comprising pridopidine or a pharmaceutically acceptable salt thereof, wherein the viral infection, disease, or disorder comprises human coronavirus, SARS, MERS coronavirus, SARS coronavirus 2, or mutations therefrom.

2. The method of claim 1, wherein the disease is COVID-19.

3. The method of claim 1, wherein the method further reduces ER stress in the subject.

4. The method of claim 2, wherein the symptoms of COVID-19 comprise, renal failure, fever, tiredness, dry cough, aches and pains, nasal congestion, runny nose, sore throat, diarrhea or combination thereof.

5. The method of claim 1, wherein the composition further comprises at least one of its analog compounds 1-7, or salts thereof:

(1)

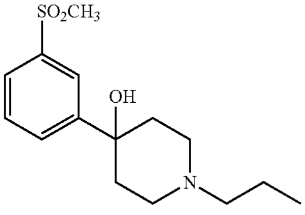

, (2)

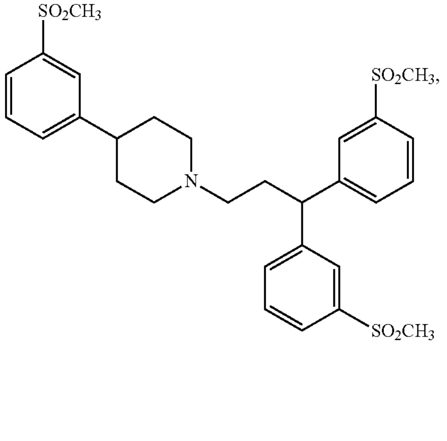

-continued (3)

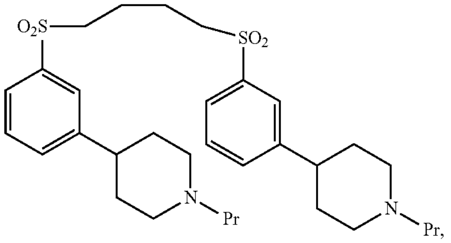

(4)

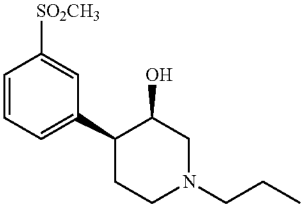

, (5)

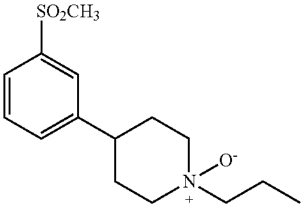

, (6)

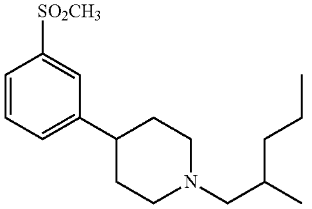

, or (7)

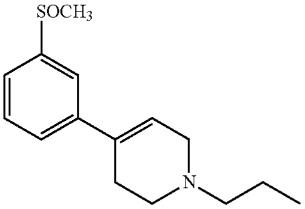

.

6. The method of claim 5, wherein the method comprises administering a composition comprising pridopidine or pharmaceutically acceptable salt thereof, in combination with compound 1 or pharmaceutically acceptable salt thereof.

7. The method of claim 5, wherein the method comprises administering a composition comprising pridopidine or pharmaceutically acceptable salt thereof in combination with compound 1 or pharmaceutically acceptable salt thereof and compound 4 or pharmaceutically acceptable salt thereof.

8. The method of claim 5, wherein the pridopidine is in a base form or a pharmaceutically acceptable salt form.

9. The method of claim 5 wherein the pridopidine salt comprises pridopidine hydrochloride, hydrobromide, hydroiodide, nitrate, sulfate, bisulfate, phosphate, acid phosphate, isonicotinate, acetate, lactate, salicylate, citrate, D,L-tartrate, L-tartarate, D-tartarate, pantothenate, bitartrate, ascorbate, succinate, hemisuccinate, maleate, gentisinate, gentisate, fumarate, gluconate, glucaronate, glycolate, saccharate, formate, besylate, benzoate, glutamate, malate, methanesulfonate, ethanesulfonate, benzensulfonate, p-toluenesulfonate, oxalate, tosylate, naphtalen-2-sulfate, or pamoate salts.

10. A method of reducing endoplasmic reticulum stress (ER stress) due to a viral infection, disease or disorder in a subject, comprising administering to the subject a composition comprising pridopidine or a pharmaceutically acceptable salt thereof, wherein the viral infection, disease, or disorder comprises human coronavirus, SARS, MERS coronavirus, SARS coronavirus 2, or mutations therefrom.

11. The method of claim 10, wherein the disease is COVID-19.

12. The method of claim 10, wherein the composition further comprises at least one of its analog compounds 1-7, or salts thereof;

(1)

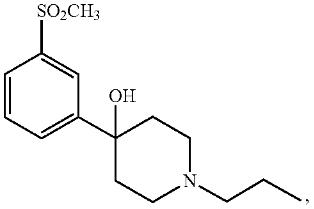

(2)

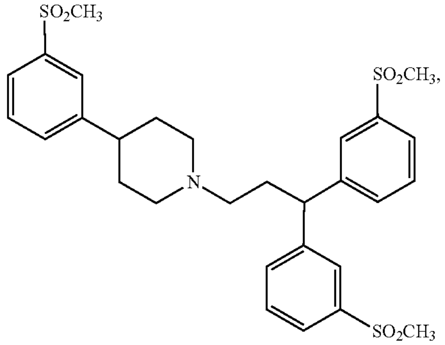

(3)

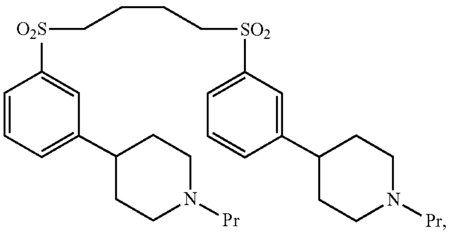

(4)

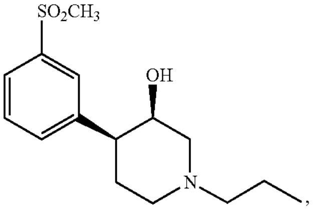

-continued (5)

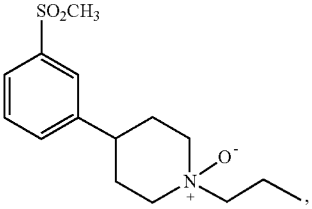

(6)

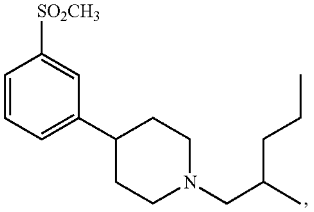

or (7)

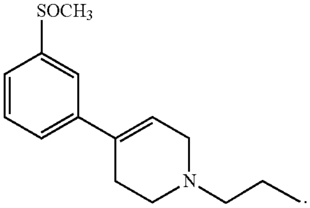

13. The method of claim 12, wherein the method comprises administering a composition comprising pridopidine or pharmaceutically acceptable salt thereof in combination with compound 1 or pharmaceutically acceptable salt thereof.

14. The method of claim 12, wherein the method comprises administering a composition comprising pridopidine or pharmaceutically acceptable salt thereof in combination with compound 1 or pharmaceutically acceptable salt thereof and compound 4 or pharmaceutically acceptable salt thereof.

15. The method of claim 12, wherein the pridopidine is in a base form or a pharmaceutically acceptable salt form.

16. The method of claim 12, wherein the pridopidine salt comprises pridopidine hydrochloride, hydrobromide, hydroiodide, nitrate, sulfate, bisulfate, phosphate, acid phosphate, isonicotinate, acetate, lactate, salicylate, citrate, D,L-tartrate, L-tartarate, D-tartarate, pantothenate, bitartrate, ascorbate, succinate, hemisuccinate, maleate, gentisinate, gentisate, fumarate, gluconate, glucaronate, glycolate, saccharate, formate, besylate, benzoate, glutamate, malate, methanesulfonate, ethanesulfonate, benzensulfonate, p-toluenesulfonate, oxalate, tosylate, naphtalen-2-sulfate, or pamoate salts.

17. The method of claim 1, wherein the pridopidine salt comprises pridopidine hydrochloride, hydrobromide, hydroiodide, nitrate, sulfate, bisulfate, phosphate, acid phosphate, isonicotinate, acetate, lactate, salicylate, citrate, D,L-tartrate, L-tartarate, D-tartarate, pantothenate, bitartrate, ascorbate, succinate, hemisuccinate, maleate, gentisinate, gentisate, fumarate, gluconate, glucaronate, glycolate, saccharate, formate, besylate, benzoate, glutamate, malate, methanesulfonate, ethanesulfonate, benzensulfonate, p-toluenesulfonate, oxalate, tosylate, naphtalen-2-sulfate, or pamoate salts.

18. The method of claim 10, wherein the pridopidine salt comprises pridopidine hydrochloride, hydrobromide, hydroiodide, nitrate, sulfate, bisulfate, phosphate, acid phosphate, isonicotinate, acetate, lactate, salicylate, citrate, D,L-tartrate, L-tartarate, D-tartarate, pantothenate, bitartrate, ascorbate, succinate, hemisuccinate, maleate, gentisinate, gentisate, fumarate, gluconate, glucaronate, glycolate, saccharate, formate, besylate, benzoate, glutamate, malate, methanesulfonate, ethanesulfonate, benzensulfonate, p-toluenesulfonate, oxalate, tosylate, naphtalen-2-sulfate, or pamoate salts.

* * * * *